US008318679B2

(12) United States Patent
Thøgersen et al.

(10) Patent No.: US 8,318,679 B2
(45) Date of Patent: *Nov. 27, 2012

(54) TRIMERISING MODULE

(75) Inventors: Hans Christian Thøgersen, Mundelstrup (DK); Michael Etzerodt, Hinnerup (DK); Thor Las Holtet, Frederikssund (DK); Niels Jonas Heilskov Graversen, Århus (DK); Jette Sandholm Kastrup, Allerød (DK); Bettina Bryde Nielsen, Greve (DK); Ingrid Kjøller Larsen, Charlottenlund (DK)

(73) Assignees: Anaphore, Inc., La Jolla, CA (US); Hoffman-La Roche, Inc., Nutley, NJ (US)

( * ) Notice: Subject to any disclaimer, the term of this patent is extended or adjusted under 35 U.S.C. 154(b) by 327 days.

This patent is subject to a terminal disclaimer.

(21) Appl. No.: 12/405,021

(22) Filed: Mar. 16, 2009

(65) Prior Publication Data

US 2010/0022756 A1    Jan. 28, 2010

Related U.S. Application Data

(63) Continuation of application No. 11/452,434, filed on Jun. 14, 2006, now Pat. No. 7,642,044, which is a continuation of application No. 09/445,576, filed as application No. PCT/DK98/00245 on Jun. 11, 1998, now abandoned.

(30) Foreign Application Priority Data

Jun. 11, 1997   (DK) .................................. 0685/97

(51) Int. Cl.
*C07K 14/00* (2006.01)
*A61K 38/16* (2006.01)
(52) U.S. Cl. ...................... 514/21.3; 530/324
(58) Field of Classification Search .................. None
See application file for complete search history.

(56) References Cited

U.S. PATENT DOCUMENTS

| 5,627,073 | A |   | 5/1997  | Baker et al.   |         |
|-----------|---|---|---------|----------------|---------|
| 6,008,023 | A | * | 12/1999 | Opper et al.   | 435/69.7|
| 6,080,400 | A | * | 6/2000  | Williams et al.| 424/93.2|

FOREIGN PATENT DOCUMENTS

| EP | 0206400    |   | 12/1986 |
|----|------------|---|---------|
| WO | 89/04209   |   | 5/1989  |
| WO | 94/18227   |   | 8/1994  |
| WO | 94/18277   |   | 8/1994  |
| WO | WO 94/18227| * | 8/1994  |
| WO | 95/31540   |   | 11/1995 |
| WO | 96/37621   |   | 11/1996 |

OTHER PUBLICATIONS

Ibragimova and Eade (Biophysical Journal, Oct. 1999, vol. 77, pp. 2191-2198).*

Hogdall et al (Clinical Chimica Acta, Feb. 17, 1997, vol. 258, pp. 159-177).*
Neilsen et al (FEBS Letters, 1997, vol. 412, pp. 388-396).*
Abstract—Berglund et al., "The gene structure of tetranectin, a plasminogen binding protein," FEBS Lett. 309(1): 15-19 (1992).
Bolivar et al., "Construction and characterization of new cloning vehicles. II. A multipurpose cloning system," Gene 2(2): 95-113 (1977).
Abstract—Carter et al., "Engineering antibodies for imaging and therapy," Curr. Opin. Biotechnol. 8(4): 449-54 (1997).
Chang et al., "Phenotypic expression in *E. coli* of a DNA sequence coding for mouse dihydrofolate reductase," Nature 275(5681): 617-24 (1978).
Chase et al., "An oncolytic viral mutant that delivers the CYP2B1 transgene and augments cyclophosphamide chemotherapy," Nat. Biotechnol. 16(5): 444-48 (1998).
Chen et al., "A polar octapeptide fused to the N-terminal fusion peptide solubilizes the influenza virus HA2 subunit ectodomain," Biochemistry 37(39): 13643-49 (1998).
Abstract—Christensen et al., "Sequence-specific binding of the N-terminal three-finger fragment of *Xenopus* transcription factor IIIA to the internal control region of a 5S RNA gene," FEBS Lett. 281(1-2): 181-84 (1991).
Abstract—Clemmensen, "Interaction of tetranectin with sulphated polysaccharides and trypan blue," Scand. J. Clin. Lab. Invest. 49(8): 719-25 (1989).
Clemmensen et al., "Purification and characterization of a novel, oligomeric, plasminogen kringle 4 binding protein from human plasma: tetranectin," Eur. J. Biochem. 156(2): 327-33 (1986).
Day, "The C-type carbohydrate recognition domain (CRD) superfamily," Biochem. Soc. Trans. 22(1): 83-88 (1994).
Debinski et al., "Novel anti-brain tumor cytotoxins specific for cancer cells," Nat. Biotechnol. 16(5): 449-53 (1998).
Abstract—Ellgaard et al., "Dissection of the domain architecture of the alpha2macroglobulin-receptor-associated protein," Eur. J. Biochem. 244(2): 544-51 (1997).
Fiers et al., "Complete nucleotide sequence of SV40 DNA," Nature 273(5658): 113-20 (1978).
Forsburg et al., "General purpose tagging vectors for fission yeast," Gene 191(2): 191-95(1997).
Abstract—Fuhlendorff, "Primary structure of tetranectin, a plasminogen kringle 4 binding plasma protein: homology with asialoglycoprotein receptors and cartilage proteoglycan core protein," Biochemistry 26(21): 6757-64 (1987).

(Continued)

*Primary Examiner* — Karen Canella
(74) *Attorney, Agent, or Firm* — McDonnell Boehnen Hulbert & Berghoff LLP

(57) ABSTRACT

The present invention relates to the design of trimeric polypeptides using polypeptide structural elements derived from the tetranectin protein family, and their use in rational de novo design and production of multi-functional molecules including the application of the multi-functional molecules in protein library technology, such as phage display technology, diagnostic and therapeutic systems, such as human gene therapy and imaging. The trimeric polypeptides being constructed as a monomer polypeptide construct comprising at least one tetranectin trimerising structural element (TTSE) which is covalently linked to at least one heterologous moiety, said TTSE being capable of forming a stable complex with two other TTSEs; or as an oligomer which is comprised of two monomer polypeptide constructs as mentioned above, and which comprises three TTSEs or a multiplum of three TTSEs, or which is comprised of three monomer polypeptide constructs.

18 Claims, 21 Drawing Sheets

OTHER PUBLICATIONS

Figure 1:
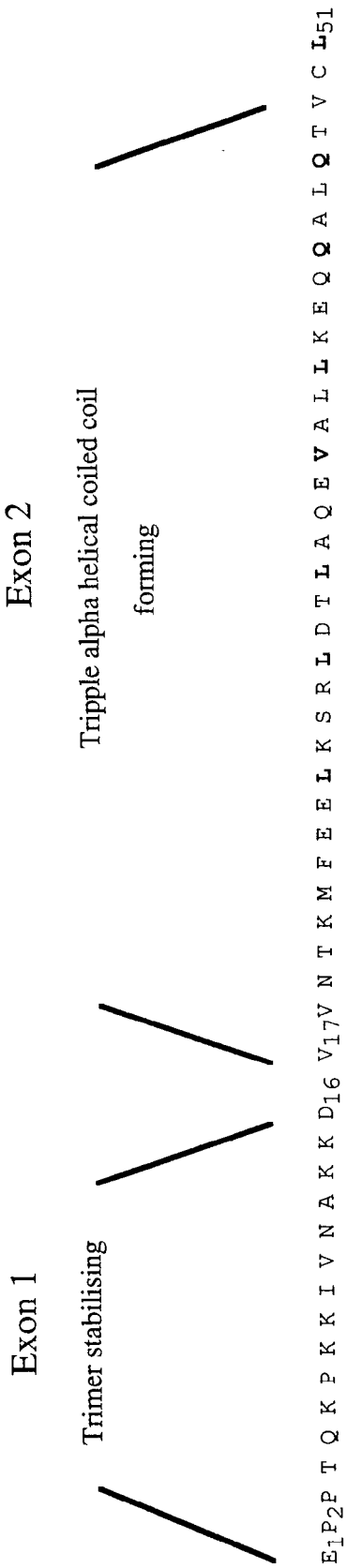

Goeddel et al., "Direct expression in *Escherichia coli* of a DNA sequence coding for human growth hormone," Nature 281(5732): 544-48 (1979).

Hess et al., "Cooperation of glycolytic enzymes," Adv. Enzyme Regul. 7: 149-67 (1969).

Hitzeman et al., "Isolation and characterization of the yeast 3-phosphoglycerokinase gene (PGK) by an immunological screening technique," J. Biol. Chem. 255(24): 12073-80 (1980).

Hochuli et al., "Genetic approach to facilitate purification of recombinant proteins with a novel metal chelate adsorbent," Bio/Technology 6: 1321-25 (1988).

Holland et al., "Isolation and identification of yeast messenger ribonucleic acids coding for enolase, glyceraldehyde-3-phosphate dehydrogenase, and phosphoglycerate kinase," Biochemistry 17(23): 4900-07 (1978).

Abstract—Holtet et al., "Tetranectin, a trimeric plasminogen-binding C-type lectin," Protein Sci. 6(7): 1511-15 (1997).

Holtet et al., "Domains and Sgared Mitifs in Plasminogen—Ligand Interaction," 21st Annual Lorne Conference on Protein Structure and Function (Melbourne, Australia) 4-8 (1996).

Ibragimova et al., "Stability of the beta-sheet of the WW domain: A molecular dynamics simulation study," Biophys. J. 77(4): 2191-98 (1999).

Ikeno et al., "Construction of YAC-based mammalian artificial chromosomes," Nat. Biotechnol. 16(5): 431-39 (1998).

Itakura et al., "Expression in *Escherichia coli* of a chemically synthesized gene for the hormone somatostatin," Science 198(4321): 1056-63 (1977).

Jones, "Proteinase mutants of *Saccharomyces cerevisiae*," Genetics 85(1): 23-33 (1977).

Kastrup et al., "Human plasminogen binding protein tetranectin: crystallization and preliminary X-ray analysis of the C-type lectin CRD and the full-length protein," Acta Crystallogr. D. Biol. Crystallogr. 53(Pt 1): 108-11 (1997).

Kim et al., "On the dynamics and conformation of the HA2 domain of the influenza virus hemagglutinin," Biochemistry 35(17): 5359-65 (1996).

Kingsman et al., "Replication in *Saccharomyces cerevisiae* of plasmid pBR313 carrying DNA from the yeast trpl region," Gene 7(2): 141-52 (1979).

Larsen et al., "Tetranectin-A Plasminogen Binding Protein," International Union of Crystallography, XVII Congress and General Assembly (Seattle, Washington), C-244, PS04.18.06, Aug. 8-17, 1996.

Lou et al., "Enhanced molecular mimicry of CEA using photoaffinity crosslinked C3d peptide," Nat. Biotechnol. 16(5): 458-62 (1998).

Mielcarek et al., "Homologous and heterologous protection after single intranasal administration of live attenuated recombinant *Bordetella pertussis*," Nat. Biotechnol. 16(5): 454-57 (1998).

Nagai et al., "Synthesis and sequence-specific proteolysis of hybrid proteins produced in *Escherichia coli*," Methods Enzymol. 153: 461-81 (1987).

Nautiyal et al., "A designed heterotrimeric coiled coil," Biochemistry 34(37): 11645-51 s(1995).

Abstract—Neame et al., "Primary structure of a protein isolated from reef shark (*Carcharhinus springeri*) cartilage that is similar to the mammalian C-type lectin homolog, tetranectin," Protein Sci. 1(1): 161-68 (1992).

Neame et al., GenBank Acc. No. P26258, "Full=Tetranectin-like protein," *Carcharhinus springeri* (reef shark), May 5, 2009 (created: May 1, 1992).

Neame et al., GenBank Acc. No. A37289, "tetranectin homolog—reef shark," *Carcharhinus springeri* (reef shark), Sep. 10, 1999.

Neame et al., GenBank Acc. No. U22298, *Bos taurus* C-type lectin homolog precursor, mRNA, complete cds., *Bos taurus* (cattle), Jun. 3, 1998.

Neame et al., "The Structure of a C-type lectin isolated from bovine cartilage," Protein Soc. Symposium (Meeting Date 1995: 9th meeting: Tech. Prot. Chem VII), Proceedings p. 401-407, (Ed., Marshak, D.R.:Publisher Academic, San Diego, Calif.).

Abstract—Nielsen et al., "Crystal structure of tetranectin, a trimeric plasminogen-binding protein with an alpha-helical coiled coil," FEBS Lett. 412(2): 388-96 (1997).

Abstract—Osbourn et al., "Generation of a panel of related human scFv antibodies with high affinities for human CEA," Immunotechnology 2(3): 181-96 (1996).

Phelan et al., "Intercellular delivery of functional p53 by the herpesvirus protein VP22," Nat. Biotechnol. 16(5): 440-43 (1998).

Abstract—Saiki et al., "Primer-directed enzymatic amplification of DNA with a thermostable DNA polymerase," Science 239(4839): 487-91 (1988).

Schaper et al., "Therapeutic targets in cardiovascular disorders," Curr. Opin. Biotechnol. 7(6): 635-40 (1996).

Schlom, "Monoclonal Antibodies: They're More and Less Than You Think," The Molecular Basis of Clinical Oncology 95-134 (1991).

Siebenlist et al., "*E. coli* RNA polymerase interacts homologously with two different promoters," Cell 20(2): 269-81 (1980).

Sorensen et al., "Cloning of a cDNA encoding murine tetranectin," Gene 152(2): 243-45 (1995).

Stinchcomb et al., "Isolation and characterisation of a yeast chromosomal replicator," Nature 282(5734): 39-43 (1979).

Studier et al., "Use of T7 RNA polymerase to direct expression of cloned genes," Methods Enzymotol. 185: 60-89 (1990).

Tschumper et al., "Sequence of a yeast DNA fragment containing a chromosomal replicator and the TRP1 gene," Gene 10(2): 157-66 (1980).

Abstract—Wewer et al., "Tetranectin, a plasminogen kringle 4-binding protein. Cloning and gene expression pattern in human colon cancer," Lab. Invest. 67(2): 253-62 (1992).

\* cited by examiner

| Position | d e f g a b c | d e f g a b c d e f g | a b c d e f g | a b c d e f g | a b c d e f g a |
|---|---|---|---|---|---|
| Human tetranectin | V V N T K M F | E E L K S R L D T L A Q | E V A L L K E | Q Q A L Q T V | C L K |
| Murine tetranectin | L V S S K M F | E E L K N R M D V L A Q | E V A L L K E | K Q A L Q T V | C L K |
| Bovine cart. protein | R R V K E K D | G D L K T Q V E K L W R | E V N A L K E | M Q A L Q T V | C L R |
| Shark cart. protein | S K S G K G K | D D L R N E I D K L W R | E V N S L K E | M Q A L Q T V | C L K |
| | | | | | |
| Consensus | L | b y L | E V L K E | Q A L Q T V C L |

Fig. 2

H6FXtripa fusion protein

1    M G S H H H H H H G S I Q G R S P G T E P P T Q K P K K I V    30

31   N A K K D V V N T K M F E E L K S R L D T L A Q E V A L L K    60

61   E Q Q A L Q T V S L K G S *    73

H6FXtripB fusion protein

1    M G S H H H H H H G S I Q G R S P G T E P P T Q K P K K I V    30

31   N A K K D V V N T K M F E E L K S R L D T L A Q E V A L L K    60

61   E Q Q A L Q T G S *    69

Fig. 4

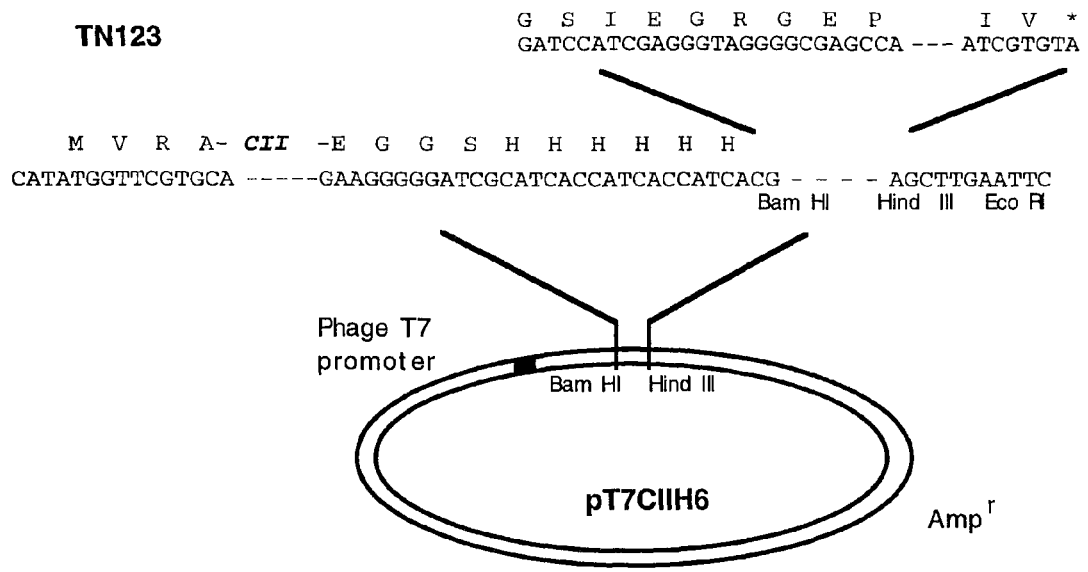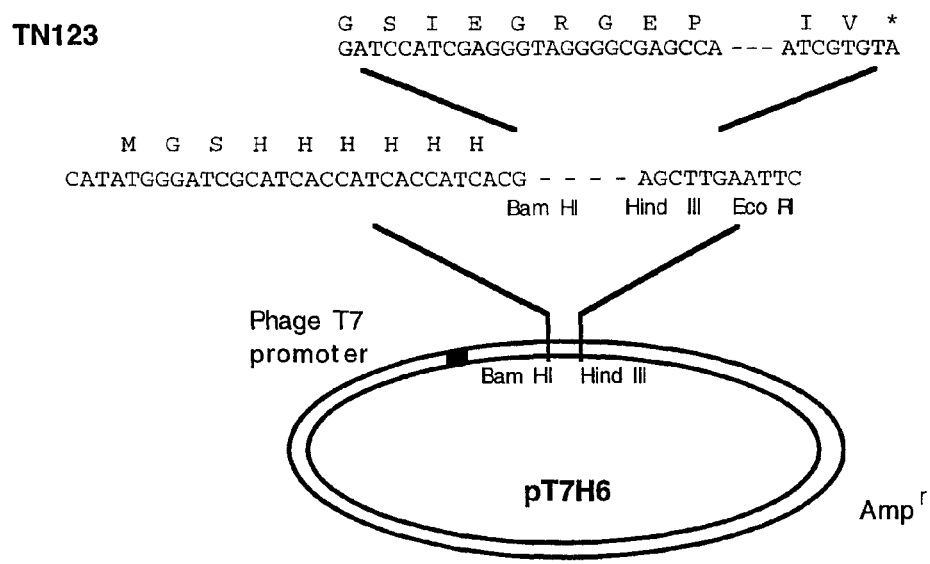
Fig. 5

CIIH6FXTN123 fusion protein

```
  1  M V R A N K R N E A L R I E S A L L N K I A M L G T E K T A   30
 31  E G G S H H H H H H G S I E G R G E P P T Q K P K K I V N A   60
 61  K K D V V N T K M F E E L K S R L D T L A Q E V A L L K E Q   90
 91  Q A L Q T V C L K G T K V H M K C F L A F T Q T K T F H E A  120
121  S E D C I S R G G T L S T P Q T G S E N D A L Y E Y L R Q S  150
151  V G N E A E I W L G L N D M A A E G T W V D M T G A R I A Y  180
181  K N W E T E I T A Q P D G G K T E N C A V L S G A A N G K W  210
211  F D K R C R D Q L P Y I C Q F G I V *                         228
```

H6FXTN123 fusion protein

```
  1  M G S H H H H H H G S I E G R G E P P T Q K P K K I V N A K   30
 31  K D V V N T K M F E E L K S R L D T L A Q E V A L L K E Q Q   60
 61  A L Q T V C L K G T K V H M K C F L A F T Q T K T F H E A S   90
 91  E D C I S R G G T L S T P Q T G S E N D A L Y E Y L R Q S V  120
121  G N E A E I W L G L N D M A A E G T W V D M T G A R I A Y K  150
151  N W E T E I T A Q P D G G K T E N C A V L S G A A N G K W F  180
181  D K R C R D Q L P Y I C Q F G I V *                           197
```

Fig. 6

H6FXTN12 fusion protein

```
  1  M G S H H H H H H G S I E G R G E P P T Q K P K K I V N A K   30
 31  K D V V N T K M F E E L K S R L D T L A Q E V A L L K E Q Q   60
 61  A L Q T V *                                                   65
```

H6FXTN23 fusion protein

```
  1  M G S H H H H H H G S I Q G R V V N T K M F E E L K S R L D   30
 31  T L A Q E V A L L K E Q Q A L Q T V C L K G T K V H M K C F   60
 61  L A F T Q T K T F H E A S E D C I S R G G T L S T P Q T G S   90
 91  E N D A L Y E Y L R Q S V G N E A E I W L G L N D M A A E G  120
121  T W V D M T G A R I A Y K N W E T E I T A Q P D G G K T E N  150
151  C A V L S G A A N G K W F D K R C R D Q L P Y I C Q F G I V  180
181  *
```

H6FXTN3 fusion protein

```
  1  M G S H H H H H H G S I E G R A L Q T V C L K G T K V H M K   30
 31  C F L A F T Q T K T F H E A S E D C I S R G G T L S T P Q T   60
 61  G S E N D A L Y E Y L R Q S V G N E A E I W L G L N D M A A   90
 91  E G T W V D M T G A R I A Y K N W E T E I T A Q P D G G K T  120
121  E N C A V L S G A A N G K W F D K R C R D Q L P Y I C Q F G  150
151  I V *                                                        152
```

Fig. 8

H6FXtripb-UB fusion protein

```
  1  M G S H H H H H H G S I Q G R S P G T E P P T Q K P K K I V    30
 31  N A K K D V V N T K M F E E L K S R L D T L A Q E V A L L K    60
 61  E Q Q A L Q T G S Q I F V K T L T G K T I T L E V E P S D T    90
 91  I E N V K A K I Q D K E G I P P D Q Q R L I F A G K Q L E D   120
121  G R T L S D Y N I Q K E S T L H L V L R L R G G S *           145
```

Fig. 14

H6FXscFv(CEA6)-tripb fusion protein

```
  1 M G S H H H H H H G S I Q G R S Q V Q L Q Q S G A E V K K P  30
 31 G S S V K V S C K A S G G T F S N S P I N W L R Q A P G Q G  60
 61 L E W M G S I I P S F G T A N Y A Q K F Q G R L T I T A D E  90
 91 S T S T A Y M E L S S L R S E D T A V Y Y C A G R S H N Y E 120
121 L Y Y Y Y M D V W G Q G T M V T V S S G G G G S G G G G S G 150
151 G G G S D I Q M T Q S P S T L S A S I G D R V T I T C R A S 180
181 E G I Y H W L A W Y Q Q K P G K A P K L L I Y K A S S L A S 210
211 G A P S R F S G S G S G T D F T L T I S S L Q P D D F A T Y 240
241 Y C Q Q Y S N Y P L T F G G G T K L E I K R A A A E Q K L I 270
271 S E E D L N G A G T E P P T Q K P K K I V N A K K D V V N T 300
301 K M F E E L K S R L D T L A Q E V A L L K E Q Q A L Q T G S 330
331 *
```

Fig. 16

H6FXtripb-scFv(CEA6) fusion protein

```
  1 M G S H H H H H H G S I Q G R S P G T E P P T Q K P K K I V  30
 31 N A K K D V V N T K M F E E L K S R L D T L A Q E V A L L K  60
 61 E Q Q A L Q T G S Q V Q L Q Q S G A E V K K P G S S V K V S  90
 91 C K A S G G T F S N S P I N W L R Q A P G Q G L E W M G S I 120
121 I P S F G T A N Y A Q K F Q G R L T I T A D E S T S T A Y M 150
151 E L S S L R S E D T A V Y Y C A G R S H N Y E L Y Y Y Y M D 180
181 V W G Q G T M V T V S S G G G G S G G G G S G G G G S D I Q 210
211 M T Q S P S T L S A S I G D R V T I T C R A S E G I Y H W L 240
241 A W Y Q Q K P G K A P K L L I Y K A S S L A S G A P S R F S 270
271 G S G S G T D F T L T I S S L Q P D D F A T Y Y C Q Q Y S N 300
301 Y P L T F G G G T K L E I K R A A A E Q K L I S E E D L N G 330
331 A *
```

Fig. 18

H6FXscFv(CEA6)-tripb-scFv(CEA6) fusion protein

```
  1 M G S H H H H H H G S I Q G R S Q V Q L Q Q S G A E V K K P  30
 31 G S S V K V S C K A S G G T F S N S P I N W L R Q A P G Q G  60
 61 L E W M G S I I P S F G T A N Y A Q K F Q G R L T I T A D E  90
 91 S T S T A Y M E L S S L R S E D T A V Y Y C A G R S H N Y E 120
121 L Y Y Y Y M D V W G Q G T M V T V S S G G G G S G G G G S G 150
151 G G G S D I Q M T Q S P S T L S A S I G D R V T I T C R A S 180
181 E G I Y H W L A W Y Q Q K P G K A P K L L I Y K A S S L A S 210
211 G A P S R F S G S G S G T D F T L T I S S L Q P D D F A T Y 240
241 Y C Q Q Y S N Y P L T F G G G T K L E I K R A A A E Q K L I 270
271 S E E D L N G A G T E P P T Q K P K K I V N A K K D V V N T 300
301 K M F E E L K S R L D T L A Q E V A L L K E Q Q A L Q T G S 330
331 Q V Q L Q Q S G A E V K K P G S S V K V S C K A S G G T F S 360
361 N S P I N W L R Q A P G Q G L E W M G S I I P S F G T A N Y 390
391 A Q K F Q G R L T I T A D E S T S T A Y M E L S S L R S E D 420
421 T A V Y Y C A G R S H N Y E L Y Y Y Y M D V W G Q G T M V T 450
451 V S S G G G G S G G G G S G G G G S D I Q M T Q S P S T L S 480
481 A S I G D R V T I T C R A S E G I Y H W L A W Y Q Q K P G K 510
511 A P K L L I Y K A S S L A S G A P S R F S G S G S G T D F T 540
541 L T I S S L Q P D D F A T Y Y C Q Q Y S N Y P L T F G G G T 570
571 K L E I K R A A A E Q K L I S E E D L N G A * 592
```

Fig. 20

SEQUENCE LISTING

<160> NUMBER OF SEQ ID NOS: 104

<210> SEQ ID NO 1
<211> LENGTH: 47
<212> TYPE: DNA
<213> ORGANISM: Artificial
<220> FEATURE:
<223> OTHER INFORMATION: primer trip-Ca

<400> SEQUENCE: 1
cctgatcaat ccagggaaga tctcctggta ccgagccacc aacccag           47

<210> SEQ ID NO 2
<211> LENGTH: 33
<212> TYPE: DNA
<213> ORGANISM: Artificial
<220> FEATURE:
<223> OTHER INFORMATION: primer trip-Ca

<400> SEQUENCE: 2
ccaagcttat taggatcccg tctgcagggc ctg                          33

<210> SEQ ID NO 3
<211> LENGTH: 40
<212> TYPE: DNA
<213> ORGANISM: Artificial
<220> FEATURE:
<223> OTHER INFORMATION: trip-Cb

<400> SEQUENCE: 3
gcgaagctta ttaggatccc ttcagggaga ccgtctgcag                   40

<210> SEQ ID NO 4
<211> LENGTH: 6
<212> TYPE: PRT
<213> ORGANISM: Artificial
<220> FEATURE:
<223> OTHER INFORMATION: IQGR cleavage site

<400> SEQUENCE: 4

Gly Ser Ile Gln Gly Arg
1               5

<210> SEQ ID NO 5
<211> LENGTH: 52
<212> TYPE: PRT
<213> ORGANISM: Artificial
<220> FEATURE:
<223> OTHER INFORMATION: tetranectin polypeptide sequence for Glu1 to
      Lys52

<400> SEQUENCE: 5

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
                20                  25                  30

Leu Ala Gln Glu Val Ala Leu Leu Lys Glu Gln Gln Ala Leu Gln Thr
            35                  40                  45

Val Ser Leu Lys
        50

<210> SEQ ID NO 6
<211> LENGTH: 49
<212> TYPE: PRT

-continued

<213> ORGANISM: Artificial
<220> FEATURE:
<223> OTHER INFORMATION: tetranectin polypeptide sequence for Glu 1 to
    Val 49

<400> SEQUENCE: 6

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val

<210> SEQ ID NO 7
<211> LENGTH: 181
<212> TYPE: PRT
<213> ORGANISM: Artificial
<220> FEATURE:
<223> OTHER INFORMATION: Mature tetranectin single chain

<400> SEQUENCE: 7

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Asp Met Ala Ala Glu Gly Thr Trp Val Asp Met Thr Gly
        115                 120                 125

Ala Arg Ile Ala Tyr Lys Asn Trp Glu Thr Glu Ile Thr Ala Gln Pro
    130                 135                 140

Asp Gly Gly Lys Thr Glu Asn Cys Ala Val Leu Ser Gly Ala Ala Asn
145                 150                 155                 160

Gly Lys Trp Phe Asp Lys Arg Cys Arg Asp Gln Leu Pro Tyr Ile Cys
                165                 170                 175

Gln Phe Gly Ile Val
            180

<210> SEQ ID NO 8
<211> LENGTH: 39
<212> TYPE: DNA
<213> ORGANISM: Artificial
<220> FEATURE:
<223> OTHER INFORMATION: Primer

<400> SEQUENCE: 8
cctggatcca tcgagggtag gggcgagcca ccaacccag                              39

<210> SEQ ID NO 9
<211> LENGTH: 25
<212> TYPE: DNA

```
<213> ORGANISM: Artificial
<220> FEATURE:
<223> OTHER INFORMATION: Primer

<400> SEQUENCE: 9
ccgaagctta cacgatcccg aactg                                              25

<210> SEQ ID NO 10
<211> LENGTH: 6
<212> TYPE: PRT
<213> ORGANISM: Artificial
<220> FEATURE:
<223> OTHER INFORMATION: IEGR cleavage site

<400> SEQUENCE: 10

Gly Ser Ile Glu Gly Arg
1               5

<210> SEQ ID NO 11
<211> LENGTH: 32
<212> TYPE: PRT
<213> ORGANISM: Artificial
<220> FEATURE:
<223> OTHER INFORMATION: lambda CII protein

<400> SEQUENCE: 11

Met Val Arg Ala Asn Lys Arg Asn Glu Ala Leu Arg Ile Glu Ser Ala
1               5                   10                  15

Leu Leu Asn Lys Ile Ala Met Leu Gly Thr Glu Lys Thr Ala Glu Gly
            20                  25                  30

<210> SEQ ID NO 12
<211> LENGTH: 10
<212> TYPE: PRT
<213> ORGANISM: Homo sapiens

<400> SEQUENCE: 12

Gly Ser His His His His His His Gly Ser
1               5                   10

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
ccgaagctta gaccgtctgc agggc                                              25

<210> SEQ ID NO 14
<211> LENGTH: 39
<212> TYPE: DNA
<213> ORGANISM: Artificial
<220> FEATURE:
<223> OTHER INFORMATION: Primer

<400> SEQUENCE: 14
ggcggatcca tccagggtag ggttgtgaac acaaagatg                               39

<210> SEQ ID NO 15
<211> LENGTH: 36
<212> TYPE: DNA
<213> ORGANISM: Artificial
<220> FEATURE:
<223> OTHER INFORMATION: Primer
```

```
<400> SEQUENCE: 15
cctggatcca tcgagggtag ggccctgcag acggtc                              36

<210> SEQ ID NO 16
<211> LENGTH: 227
<212> TYPE: DNA
<213> ORGANISM: Homo sapiens

<400> SEQUENCE: 16
atgcagatct ttgtgaagac cctcactggc aaaaccatca cccttgaggt cgagcccagt    60
gacaccattg agaatgtcaa agccaaaatt caagacaagg agggtatccc acctgaccgc   120
agcgtctgat atttgccggc aaacagctgg aagatggacg tactttgtct gactacaata   180
ttcaaaagga gtctactctt catcttgtgt tgagacttcg tggtggt                227

<210> SEQ ID NO 17
<211> LENGTH: 27
<212> TYPE: DNA
<213> ORGANISM: Artificial
<220> FEATURE:
<223> OTHER INFORMATION: Primer

<400> SEQUENCE: 17
tgctgatcac agatctttgt gaagacc                                        27

<210> SEQ ID NO 18
<211> LENGTH: 39
<212> TYPE: DNA
<213> ORGANISM: Artificial
<220> FEATURE:
<223> OTHER INFORMATION: Primer

<400> SEQUENCE: 18
cgcaagcttg catgcttagg atccaccacg aagtctcaa                           39

<210> SEQ ID NO 19
<211> LENGTH: 76
<212> TYPE: PRT
<213> ORGANISM: Homo sapiens

<400> SEQUENCE: 19

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 20
<211> LENGTH: 786
<212> TYPE: DNA
<213> ORGANISM: Artificial
<220> FEATURE:
<223> OTHER INFORMATION: CEA6 antibody

<400> SEQUENCE: 20
caggttcagc tgcagcagtc aggggctgag gtgaagaagc ctgggtcctc ggtgaaggtc    60
tcctgcaagg cttctggagg caccttcagc aactctccta tcaactggct gcgacaggcc   120
```

-continued

```
cccggacaag ggcttgagtg gatgggaagt atcatcccctt cctttggtac agcaaactac    180
gctcagaagt tccagggcag actcacgatt accgcggacg aatccacgag cacagcctac    240
atggagctga gcagcctgag atctgaggac acggccgtgt attactgtgc ggggcggagc    300
cacaactacg aactctacta ttactacatg gacgtctggg gccaggggac aatggtcacc    360
gtctcgagtg gtggaggcgg ttcaggcgga ggtggcagcg gcggtggcgg atcggacatc    420
cagatgaccc agtctccttc caccctgtct gcatctattg gagacagagt caccatcacc    480
tgccgggcca gtgagggtat ttatcactgg ttggcctggt atcagcagaa gccagggaaa    540
gcccctaaac tcctgatcta taaggcctct agtttagcca gtggggcccc atcaaggttc    600
agcggcagtg gatctgggac agatttcact ctcaccatca gcagcctgca gcctgatgat    660
tttgcaactt attactgcca acaatatagt aattatccgc tcactttcgg cggagggacc    720
aagctggaga tcaaacgtgc ggccgcagaa caaaaactca tctcagaaga ggatctgaat    780
ggggcc                                                                786
```

<210> SEQ ID NO 21
<211> LENGTH: 25
<212> TYPE: DNA
<213> ORGANISM: Artificial
<220> FEATURE:
<223> OTHER INFORMATION: Primer

<400> SEQUENCE: 21
ggtggatccc aggttcagct gcagc                25

<210> SEQ ID NO 22
<211> LENGTH: 25
<212> TYPE: DNA
<213> ORGANISM: Artificial
<220> FEATURE:
<223> OTHER INFORMATION: Primer

<400> SEQUENCE: 22
gccggtaccg gccccattca gatcc                25

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23
tccaagctta ggccccattc agatcc               26

<210> SEQ ID NO 24
<211> LENGTH: 228
<212> TYPE: PRT
<213> ORGANISM: Artificial
<220> FEATURE:
<223> OTHER INFORMATION: CIIH6FXTN123

<400> SEQUENCE: 24

Met Val Arg Ala Asn Lys Arg Asn Glu Ala Leu Arg Ile Glu Ser Ala
1               5                   10                  15

Leu Leu Asn Lys Ile Ala Met Leu Gly Thr Glu Lys Thr Ala Glu Gly
                20                  25                  30

Gly Ser His His His His His His Gly Ser Ile Glu Gly Arg Gly Glu
            35                  40                  45

```
Pro Pro Thr Gln Lys Pro Lys Lys Ile Val Asn Ala Lys Lys Asp Val
 50                  55                  60

Val Asn Thr Lys Met Phe Glu Glu Leu Lys Ser Arg Leu Asp Thr Leu
 65                  70                  75                  80

Ala Gln Glu Val Ala Leu Leu Lys Glu Gln Gln Ala Leu Gln Thr Val
                 85                  90                  95

Cys Leu Lys Gly Thr Lys Val His Met Lys Cys Phe Leu Ala Phe Thr
            100                 105                 110

Gln Thr Lys Thr Phe His Glu Ala Ser Glu Asp Cys Ile Ser Arg Gly
        115                 120                 125

Gly Thr Leu Ser Thr Pro Gln Thr Gly Ser Glu Asn Asp Ala Leu Tyr
    130                 135                 140

Glu Tyr Leu Arg Gln Ser Val Gly Asn Glu Ala Glu Ile Trp Leu Gly
145                 150                 155                 160

Leu Asn Asp Met Ala Ala Glu Gly Thr Trp Val Asp Met Thr Gly Ala
                165                 170                 175

Arg Ile Ala Tyr Lys Asn Trp Glu Thr Glu Ile Thr Ala Gln Pro Asp
            180                 185                 190

Gly Gly Lys Thr Glu Asn Cys Ala Val Leu Ser Gly Ala Ala Asn Gly
        195                 200                 205

Lys Trp Phe Asp Lys Arg Cys Arg Asp Gln Leu Pro Tyr Ile Cys Gln
    210                 215                 220

Phe Gly Ile Val
225

<210> SEQ ID NO 25
<211> LENGTH: 197
<212> TYPE: PRT
<213> ORGANISM: Artificial
<220> FEATURE:
<223> OTHER INFORMATION: H6FXTN123

<400> SEQUENCE: 25

Met Gly Ser His His His His His His Gly Ser Ile Glu Gly Arg Gly
 1               5                  10                  15

Glu Pro Pro Thr Gln Lys Pro Lys Lys Ile Val Asn Ala Lys Lys Asp
                 20                  25                  30

Val Val Asn Thr Lys Met Phe Glu Glu Leu Lys Ser Arg Leu Asp Thr
             35                  40                  45

Leu Ala Gln Glu Val Ala Leu Leu Lys Glu Gln Gln Ala Leu Gln Thr
         50                  55                  60

Val Cys Leu Lys Gly Thr Lys Val His Met Lys Cys Phe Leu Ala Phe
 65                  70                  75                  80

Thr Gln Thr Lys Thr Phe His Glu Ala Ser Glu Asp Cys Ile Ser Arg
                 85                  90                  95

Gly Gly Thr Leu Ser Thr Pro Gln Thr Gly Ser Glu Asn Asp Ala Leu
            100                 105                 110

Tyr Glu Tyr Leu Arg Gln Ser Val Gly Asn Glu Ala Glu Ile Trp Leu
        115                 120                 125

Gly Leu Asn Asp Met Ala Ala Glu Gly Thr Trp Val Asp Met Thr Gly
    130                 135                 140

Ala Arg Ile Ala Tyr Lys Asn Trp Glu Thr Glu Ile Thr Ala Gln Pro
145                 150                 155                 160

Asp Gly Gly Lys Thr Glu Asn Cys Ala Val Leu Ser Gly Ala Ala Asn
                165                 170                 175

Gly Lys Trp Phe Asp Lys Arg Cys Arg Asp Gln Leu Pro Tyr Ile Cys
```

```
                    180                 185                 190

Gln Phe Gly Ile Val
            195

<210> SEQ ID NO 26
<211> LENGTH: 65
<212> TYPE: PRT
<213> ORGANISM: Artificial
<220> FEATURE:
<223> OTHER INFORMATION: H6FXTN12

<400> SEQUENCE: 26

Met Gly Ser His His His His His Gly Ser Ile Glu Gly Arg Gly
1               5                   10                  15

Glu Pro Pro Thr Gln Lys Pro Lys Lys Ile Val Asn Ala Lys Lys Asp
            20                  25                  30

Val Val Asn Thr Lys Met Phe Glu Glu Leu Lys Ser Arg Leu Asp Thr
        35                  40                  45

Leu Ala Gln Glu Val Ala Leu Leu Lys Glu Gln Gln Ala Leu Gln Thr
    50                  55                  60

Val
65

<210> SEQ ID NO 27
<211> LENGTH: 180
<212> TYPE: PRT
<213> ORGANISM: Artificial
<220> FEATURE:
<223> OTHER INFORMATION: H6FXTN23

<400> SEQUENCE: 27

Met Gly Ser His His His His His Gly Ser Ile Gln Gly Arg Val
1               5                   10                  15

Val Asn Thr Lys Met Phe Glu Glu Leu Lys Ser Arg Leu Asp Thr Leu
            20                  25                  30

Ala Gln Glu Val Ala Leu Leu Lys Glu Gln Gln Ala Leu Gln Thr Val
        35                  40                  45

Cys Leu Lys Gly Thr Lys Val His Met Lys Cys Phe Leu Ala Phe Thr
    50                  55                  60

Gln Thr Lys Thr Phe His Glu Ala Ser Glu Asp Cys Ile Ser Arg Gly
65                  70                  75                  80

Gly Thr Leu Ser Thr Pro Gln Thr Gly Ser Glu Asn Asp Ala Leu Tyr
                85                  90                  95

Glu Tyr Leu Arg Gln Ser Val Gly Asn Glu Ala Glu Ile Trp Leu Gly
            100                 105                 110

Leu Asn Asp Met Ala Ala Glu Gly Thr Trp Val Asp Met Thr Gly Ala
        115                 120                 125

Arg Ile Ala Tyr Lys Asn Trp Glu Thr Glu Ile Thr Ala Gln Pro Asp
    130                 135                 140

Gly Gly Lys Thr Glu Asn Cys Ala Val Leu Ser Gly Ala Ala Asn Gly
145                 150                 155                 160

Lys Trp Phe Asp Lys Arg Cys Arg Asp Gln Leu Pro Tyr Ile Cys Gln
                165                 170                 175

Phe Gly Ile Val
            180

<210> SEQ ID NO 28
<211> LENGTH: 73
<212> TYPE: PRT
```

<213> ORGANISM: Artificial
<220> FEATURE:
<223> OTHER INFORMATION: H6FXtripa

<400> SEQUENCE: 28

```
Met Gly Ser His His His His His Gly Ser Ile Gln Gly Arg Ser
1               5                   10                  15

Pro Gly Thr Glu Pro Pro Thr Gln Lys Pro Lys Lys Ile Val Asn Ala
            20                  25                  30

Lys Lys Asp Val Val Asn Thr Lys Met Phe Glu Glu Leu Lys Ser Arg
        35                  40                  45

Leu Asp Thr Leu Ala Gln Glu Val Ala Leu Leu Lys Glu Gln Gln Ala
    50                  55                  60

Leu Gln Thr Val Ser Leu Lys Gly Ser
65                  70
```

<210> SEQ ID NO 29
<211> LENGTH: 69
<212> TYPE: PRT
<213> ORGANISM: Artificial
<220> FEATURE:
<223> OTHER INFORMATION: H6FXtripb

<400> SEQUENCE: 29

```
Met Gly Ser His His His His His Gly Ser Ile Gln Gly Arg Ser
1               5                   10                  15

Pro Gly Thr Glu Pro Pro Thr Gln Lys Pro Lys Lys Ile Val Asn Ala
            20                  25                  30

Lys Lys Asp Val Val Asn Thr Lys Met Phe Glu Glu Leu Lys Ser Arg
        35                  40                  45

Leu Asp Thr Leu Ala Gln Glu Val Ala Leu Leu Lys Glu Gln Gln Ala
    50                  55                  60

Leu Gln Thr Gly Ser
65
```

<210> SEQ ID NO 30
<211> LENGTH: 152
<212> TYPE: PRT
<213> ORGANISM: Artificial
<220> FEATURE:
<223> OTHER INFORMATION: H6FXTN3

<400> SEQUENCE: 30

```
Met Gly Ser His His His His His Gly Ser Ile Glu Gly Arg Ala
1               5                   10                  15

Leu Gln Thr Val Cys Leu Lys Gly Thr Lys Val His Met Lys Cys Phe
            20                  25                  30

Leu Ala Phe Thr Gln Thr Lys Thr Phe His Glu Ala Ser Glu Asp Cys
        35                  40                  45

Ile Ser Arg Gly Gly Thr Leu Ser Thr Pro Gln Thr Gly Ser Glu Asn
    50                  55                  60

Asp Ala Leu Tyr Glu Tyr Leu Arg Gln Ser Val Gly Asn Glu Ala Glu
65                  70                  75                  80

Ile Trp Leu Gly Leu Asn Asp Met Ala Ala Glu Gly Thr Trp Val Asp
            85                  90                  95

Met Thr Gly Ala Arg Ile Ala Tyr Lys Asn Trp Glu Thr Glu Ile Thr
            100                 105                 110

Ala Gln Pro Asp Gly Gly Lys Thr Glu Asn Cys Ala Val Leu Ser Gly
        115                 120                 125
```

Ala Ala Asn Gly Lys Trp Phe Asp Lys Arg Cys Arg Asp Gln Leu Pro
            130                 135                 140

Tyr Ile Cys Gln Phe Gly Ile Val
145                 150

<210> SEQ ID NO 31
<211> LENGTH: 145
<212> TYPE: PRT
<213> ORGANISM: Artificial
<220> FEATURE:
<223> OTHER INFORMATION: H6FXtripb-UB

<400> SEQUENCE: 31

Met Gly Ser His His His His His Gly Ser Ile Gln Gly Arg Ser
1               5                   10                  15

Pro Gly Thr Glu Pro Pro Thr Gln Lys Pro Lys Ile Val Asn Ala
            20                  25                  30

Lys Lys Asp Val Val Asn Thr Lys Met Phe Glu Glu Leu Lys Ser Arg
            35                  40                  45

Leu Asp Thr Leu Ala Gln Glu Val Ala Leu Leu Lys Glu Gln Gln Ala
        50                  55                  60

Leu Gln Thr Gly Ser Gln Ile Phe Val Lys Thr Leu Thr Gly Lys Thr
65                  70                  75                  80

Ile Thr Leu Glu Val Glu Pro Ser Asp Thr Ile Glu Asn Val Lys Ala
                85                  90                  95

Lys Ile Gln Asp Lys Glu Gly Ile Pro Pro Asp Gln Gln Arg Leu Ile
            100                 105                 110

Phe Ala Gly Lys Gln Leu Glu Asp Gly Arg Thr Leu Ser Asp Tyr Asn
        115                 120                 125

Ile Gln Lys Glu Ser Thr Leu His Leu Val Leu Arg Leu Arg Gly Gly
    130                 135                 140

Ser
145

<210> SEQ ID NO 32
<211> LENGTH: 330
<212> TYPE: PRT
<213> ORGANISM: Artificial
<220> FEATURE:
<223> OTHER INFORMATION: H6FXscFv(CEA6)-TRIPB

<400> SEQUENCE: 32

Met Gly Ser His His His His His Gly Ser Ile Gln Gly Arg Ser
1               5                   10                  15

Gln Val Gln Leu Gln Gln Ser Gly Ala Glu Val Lys Lys Pro Gly Ser
            20                  25                  30

Ser Val Lys Val Ser Cys Lys Ala Ser Gly Gly Thr Phe Ser Asn Ser
        35                  40                  45

Pro Ile Asn Trp Leu Arg Gln Ala Pro Gly Gln Gly Leu Glu Trp Met
        50                  55                  60

Gly Ser Ile Ile Pro Ser Phe Gly Thr Ala Asn Tyr Ala Gln Lys Phe
65                  70                  75                  80

Gln Gly Arg Leu Thr Ile Thr Ala Asp Glu Ser Thr Ser Thr Ala Tyr
                85                  90                  95

Met Glu Leu Ser Ser Leu Arg Ser Glu Asp Thr Ala Val Tyr Tyr Cys
            100                 105                 110

Ala Gly Arg Ser His Asn Tyr Glu Leu Tyr Tyr Tyr Met Asp Val
        115                 120                 125

```
Trp Gly Gln Gly Thr Met Val Thr Val Ser Ser Gly Gly Gly Ser
        130                 135                 140
Gly Gly Gly Gly Ser Gly Gly Gly Ser Asp Ile Gln Met Thr Gln
145                 150                 155                 160
Ser Pro Ser Thr Leu Ser Ala Ser Ile Gly Asp Arg Val Thr Ile
                165                 170                 175
Cys Arg Ala Ser Glu Gly Ile Tyr His Trp Leu Ala Trp Tyr Gln Gln
            180                 185                 190
Lys Pro Gly Lys Ala Pro Lys Leu Leu Ile Tyr Lys Ala Ser Ser Leu
        195                 200                 205
Ala Ser Gly Ala Pro Ser Arg Phe Ser Gly Ser Gly Ser Gly Thr Asp
    210                 215                 220
Phe Thr Leu Thr Ile Ser Ser Leu Gln Pro Asp Asp Phe Ala Thr Tyr
225                 230                 235                 240
Tyr Cys Gln Gln Tyr Ser Asn Tyr Pro Leu Thr Phe Gly Gly Gly Thr
                245                 250                 255
Lys Leu Glu Ile Lys Arg Ala Ala Ala Glu Gln Lys Leu Ile Ser Glu
            260                 265                 270
Glu Asp Leu Asn Gly Ala Gly Thr Glu Pro Pro Thr Gln Lys Pro Lys
        275                 280                 285
Lys Ile Val Asn Ala Lys Lys Asp Val Val Asn Thr Lys Met Phe Glu
    290                 295                 300
Glu Leu Lys Ser Arg Leu Asp Thr Leu Ala Gln Glu Val Ala Leu Leu
305                 310                 315                 320
Lys Glu Gln Gln Ala Leu Gln Thr Gly Ser
                325                 330

<210> SEQ ID NO 33
<211> LENGTH: 331
<212> TYPE: PRT
<213> ORGANISM: Artificial
<220> FEATURE:
<223> OTHER INFORMATION: H6FXTRIPB-scFv(CEA6)

<400> SEQUENCE: 33

Met Gly Ser His His His His His His Gly Ser Ile Gln Gly Arg Ser
1               5                   10                  15
Pro Gly Thr Glu Pro Pro Thr Gln Lys Pro Lys Lys Ile Val Asn Ala
            20                  25                  30
Lys Lys Asp Val Val Asn Thr Lys Met Phe Glu Glu Leu Lys Ser Arg
        35                  40                  45
Leu Asp Thr Leu Ala Gln Glu Val Ala Leu Leu Lys Glu Gln Gln Ala
    50                  55                  60
Leu Gln Thr Gly Ser Gln Val Gln Leu Gln Gln Ser Gly Ala Glu Val
65                  70                  75                  80
Lys Lys Pro Gly Ser Ser Val Lys Val Ser Cys Lys Ala Ser Gly Gly
                85                  90                  95
Thr Phe Ser Asn Ser Pro Ile Asn Trp Leu Arg Gln Ala Pro Gly Gln
            100                 105                 110
Gly Leu Glu Trp Met Gly Ser Ile Ile Pro Ser Phe Gly Thr Ala Asn
        115                 120                 125
Tyr Ala Gln Lys Phe Gln Gly Arg Leu Thr Ile Thr Ala Asp Glu Ser
    130                 135                 140
Thr Ser Thr Ala Tyr Met Glu Leu Ser Ser Leu Arg Ser Glu Asp Thr
145                 150                 155                 160
Ala Val Tyr Tyr Cys Ala Gly Arg Ser His Asn Tyr Glu Leu Tyr Tyr
```

```
                    165                 170                 175
Tyr Tyr Met Asp Val Trp Gly Gln Gly Thr Met Val Thr Val Ser Ser
            180                 185                 190

Gly Gly Gly Gly Ser Gly Gly Gly Ser Gly Gly Gly Ser Asp
            195                 200                 205

Ile Gln Met Thr Gln Ser Pro Ser Thr Leu Ser Ala Ser Ile Gly Asp
            210                 215                 220

Arg Val Thr Ile Thr Cys Arg Ala Ser Glu Gly Ile Tyr His Trp Leu
225                 230                 235                 240

Ala Trp Tyr Gln Gln Lys Pro Gly Lys Ala Pro Lys Leu Leu Ile Tyr
                245                 250                 255

Lys Ala Ser Ser Leu Ala Ser Gly Ala Pro Ser Arg Phe Ser Gly Ser
                260                 265                 270

Gly Ser Gly Thr Asp Phe Thr Leu Thr Ile Ser Ser Leu Gln Pro Asp
            275                 280                 285

Asp Phe Ala Thr Tyr Tyr Cys Gln Gln Tyr Ser Asn Tyr Pro Leu Thr
            290                 295                 300

Phe Gly Gly Gly Thr Lys Leu Glu Ile Lys Arg Ala Ala Ala Glu Gln
305                 310                 315                 320

Lys Leu Ile Ser Glu Glu Asp Leu Asn Gly Ala
                325                 330

<210> SEQ ID NO 34
<211> LENGTH: 592
<212> TYPE: PRT
<213> ORGANISM: Artificial
<220> FEATURE:
<223> OTHER INFORMATION: H6FXscFv(CEA6)tripbscFv(CEA6)

<400> SEQUENCE: 34

Met Gly Ser His His His His His His Gly Ser Ile Gln Gly Arg Ser
1               5                   10                  15

Gln Val Gln Leu Gln Gln Ser Gly Ala Glu Val Lys Lys Pro Gly Ser
            20                  25                  30

Ser Val Lys Val Ser Cys Lys Ala Ser Gly Gly Thr Phe Ser Asn Ser
        35                  40                  45

Pro Ile Asn Trp Leu Arg Gln Ala Pro Gly Gln Gly Leu Glu Trp Met
    50                  55                  60

Gly Ser Ile Ile Pro Ser Phe Gly Thr Ala Asn Tyr Ala Gln Lys Phe
65                  70                  75                  80

Gln Gly Arg Leu Thr Ile Thr Ala Asp Glu Ser Thr Ser Thr Ala Tyr
                85                  90                  95

Met Glu Leu Ser Ser Leu Arg Ser Glu Asp Thr Ala Val Tyr Tyr Cys
            100                 105                 110

Ala Gly Arg Ser His Asn Tyr Glu Leu Tyr Tyr Tyr Met Asp Val
        115                 120                 125

Trp Gly Gln Gly Thr Met Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Thr Leu Ser Ala Ser Ile Gly Asp Arg Val Thr Ile Thr
                165                 170                 175

Cys Arg Ala Ser Glu Gly Ile Tyr His Trp Leu Ala Trp Tyr Gln Gln
            180                 185                 190

Lys Pro Gly Lys Ala Pro Lys Leu Leu Ile Tyr Lys Ala Ser Ser Leu
        195                 200                 205
```

Ala Ser Gly Ala Pro Ser Arg Phe Ser Gly Ser Gly Ser Gly Thr Asp
            210                 215                 220
Phe Thr Leu Thr Ile Ser Ser Leu Gln Pro Asp Asp Phe Ala Thr Tyr
225                 230                 235                 240
Tyr Cys Gln Gln Tyr Ser Asn Tyr Pro Leu Thr Phe Gly Gly Gly Thr
                245                 250                 255
Lys Leu Glu Ile Lys Arg Ala Ala Ala Glu Gln Lys Leu Ile Ser Glu
            260                 265                 270
Glu Asp Leu Asn Gly Ala Gly Thr Glu Pro Pro Thr Gln Lys Pro Lys
            275                 280                 285
Lys Ile Val Asn Ala Lys Lys Asp Val Val Asn Thr Lys Met Phe Glu
290                 295                 300
Glu Leu Lys Ser Arg Leu Asp Thr Leu Ala Gln Glu Val Ala Leu Leu
305                 310                 315                 320
Lys Glu Gln Gln Ala Leu Gln Thr Gly Ser Gln Val Gln Leu Gln Gln
            325                 330                 335
Ser Gly Ala Glu Val Lys Lys Pro Gly Ser Ser Val Lys Val Ser Cys
            340                 345                 350
Lys Ala Ser Gly Gly Thr Phe Ser Asn Ser Pro Ile Asn Trp Leu Arg
            355                 360                 365
Gln Ala Pro Gly Gln Gly Leu Glu Trp Met Gly Ser Ile Ile Pro Ser
            370                 375                 380
Phe Gly Thr Ala Asn Tyr Ala Gln Lys Phe Gln Gly Arg Leu Thr Ile
385                 390                 395                 400
Thr Ala Asp Glu Ser Thr Ser Thr Ala Tyr Met Glu Leu Ser Ser Leu
            405                 410                 415
Arg Ser Glu Asp Thr Ala Val Tyr Tyr Cys Ala Gly Arg Ser His Asn
            420                 425                 430
Tyr Glu Leu Tyr Tyr Tyr Met Asp Val Trp Gly Gln Gly Thr Met
            435                 440                 445
Val Thr Val Ser Ser Gly Gly Gly Ser Gly Gly Gly Ser Gly
450                 455                 460
Gly Gly Gly Ser Asp Ile Gln Met Thr Gln Ser Pro Ser Thr Leu Ser
465                 470                 475                 480
Ala Ser Ile Gly Asp Arg Val Thr Ile Thr Cys Arg Ala Ser Glu Gly
            485                 490                 495
Ile Tyr His Trp Leu Ala Trp Tyr Gln Gln Lys Pro Gly Lys Ala Pro
            500                 505                 510
Lys Leu Leu Ile Tyr Lys Ala Ser Ser Leu Ala Ser Gly Ala Pro Ser
            515                 520                 525
Arg Phe Ser Gly Ser Gly Ser Gly Thr Asp Phe Thr Leu Thr Ile Ser
            530                 535                 540
Ser Leu Gln Pro Asp Asp Phe Ala Thr Tyr Tyr Cys Gln Gln Tyr Ser
545                 550                 555                 560
Asn Tyr Pro Leu Thr Phe Gly Gly Gly Thr Lys Leu Glu Ile Lys Arg
                565                 570                 575
Ala Ala Ala Glu Gln Lys Leu Ile Ser Glu Glu Asp Leu Asn Gly Ala
            580                 585                 590

<210> SEQ ID NO 35
<211> LENGTH: 51
<212> TYPE: PRT
<213> ORGANISM: Homo sapiens

<400> SEQUENCE: 35

```
Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu
        50
```

<210> SEQ ID NO 36
<211> LENGTH: 36
<212> TYPE: PRT
<213> ORGANISM: Homo sapiens

<400> SEQUENCE: 36

```
Val Val Asn Thr Lys Met Phe Glu Glu Leu Lys Ser Arg Leu Asp Thr
1               5                   10                  15

Leu Ala Gln Glu Val Ala Leu Leu Lys Glu Gln Gln Ala Leu Gln Thr
            20                  25                  30

Val Cys Leu Lys
        35
```

<210> SEQ ID NO 37
<211> LENGTH: 36
<212> TYPE: PRT
<213> ORGANISM: Murine

<400> SEQUENCE: 37

```
Leu Val Ser Ser Lys Met Phe Glu Glu Leu Lys Asn Arg Met Asp Val
1               5                   10                  15

Leu Ala Gln Glu Val Ala Leu Leu Lys Glu Lys Gln Ala Leu Gln Thr
            20                  25                  30

Val Cys Leu Lys
        35
```

<210> SEQ ID NO 38
<211> LENGTH: 36
<212> TYPE: PRT
<213> ORGANISM: Bovine

<400> SEQUENCE: 38

```
Arg Arg Val Lys Glu Lys Asp Gly Asp Leu Lys Thr Gln Val Glu Lys
1               5                   10                  15

Leu Trp Arg Glu Val Asn Ala Leu Lys Glu Met Gln Ala Leu Gln Thr
            20                  25                  30

Val Cys Leu Arg
        35
```

<210> SEQ ID NO 39
<211> LENGTH: 36
<212> TYPE: PRT
<213> ORGANISM: Shark

<400> SEQUENCE: 39

```
Ser Lys Ser Gly Lys Gly Lys Asp Asp Leu Arg Asn Glu Ile Asp Lys
1               5                   10                  15

Leu Trp Arg Glu Val Asn Ser Leu Lys Glu Met Gln Ala Leu Gln Thr
            20                  25                  30

Val Cys Leu Lys
        35
```

```
<210> SEQ ID NO 40
<211> LENGTH: 36
<212> TYPE: PRT
<213> ORGANISM: Artificial
<220> FEATURE:
<223> OTHER INFORMATION: Consencus sequence
<220> FEATURE:
<221> NAME/KEY: MISC_FEATURE
<222> LOCATION: (1)..(9)
<223> OTHER INFORMATION: variable
<220> FEATURE:
<221> NAME/KEY: MISC_FEATURE
<222> LOCATION: (11)..(16)
<223> OTHER INFORMATION: variable
<220> FEATURE:
<221> NAME/KEY: MISC_FEATURE
<222> LOCATION: (18)..(19)
<223> OTHER INFORMATION: variable
<220> FEATURE:
<221> NAME/KEY: MISC_FEATURE
<222> LOCATION: (22)..(23)
<223> OTHER INFORMATION: variable
<220> FEATURE:
<221> NAME/KEY: MISC_FEATURE
<222> LOCATION: (27)..(27)
<223> OTHER INFORMATION: variable
<220> FEATURE:
<221> NAME/KEY: MISC_FEATURE
<222> LOCATION: (36)..(36)
<223> OTHER INFORMATION: variable

<400> SEQUENCE: 40

Xaa Xaa Xaa Xaa Xaa Xaa Xaa Xaa Xaa Leu Xaa Xaa Xaa Xaa Xaa Xaa
 1               5                  10                  15

Leu Xaa Xaa Glu Val Xaa Xaa Leu Lys Glu Xaa Gln Ala Leu Gln Thr
             20                  25                  30

Val Cys Leu Xaa
         35

<210> SEQ ID NO 41
<211> LENGTH: 41
<212> TYPE: DNA
<213> ORGANISM: Artificial
<220> FEATURE:
<223> OTHER INFORMATION: tripa

<400> SEQUENCE: 41
gatcaatcca gggaagatct cctggtaccg agccaccaac c              41

<210> SEQ ID NO 42
<211> LENGTH: 24
<212> TYPE: DNA
<213> ORGANISM: Artificial
<220> FEATURE:
<223> OTHER INFORMATION: tripa

<400> SEQUENCE: 42
acggtctccc tgaagggatc ctaa                                 24

<210> SEQ ID NO 43
<211> LENGTH: 41
<212> TYPE: DNA
<213> ORGANISM: Artificial
<220> FEATURE:
<223> OTHER INFORMATION: tripb

<400> SEQUENCE: 43
gatcaatcca gggaagatct cctggtaccg agccaccaac c              41
```

<210> SEQ ID NO 44
<211> LENGTH: 21
<212> TYPE: DNA
<213> ORGANISM: Artificial
<220> FEATURE:
<223> OTHER INFORMATION: tripb

<400> SEQUENCE: 44
gccctgcaga cgggatccta a                                        21

<210> SEQ ID NO 45
<211> LENGTH: 31
<212> TYPE: DNA
<213> ORGANISM: Artificial
<220> FEATURE:
<223> OTHER INFORMATION: pT7H6

<400> SEQUENCE: 45
catatgggat cgcatcacca tcaccatcac g                             31

<210> SEQ ID NO 46
<211> LENGTH: 11
<212> TYPE: DNA
<213> ORGANISM: Artificial
<220> FEATURE:
<223> OTHER INFORMATION: pT7H6

<400> SEQUENCE: 46
agcttgaatt c                                                   11

<210> SEQ ID NO 47
<211> LENGTH: 26
<212> TYPE: DNA
<213> ORGANISM: Artificial
<220> FEATURE:
<223> OTHER INFORMATION: TN123

<400> SEQUENCE: 47
gatccatcga gggtaggggc gagcca                                   26

<210> SEQ ID NO 48
<211> LENGTH: 8
<212> TYPE: DNA
<213> ORGANISM: Artificial
<220> FEATURE:
<223> OTHER INFORMATION: tn123

<400> SEQUENCE: 48 atcgtgta                                                        8

<210> SEQ ID NO 49
<211> LENGTH: 15
<212> TYPE: DNA
<213> ORGANISM: Artificial
<220> FEATURE:
<223> OTHER INFORMATION: pT7CIIH6

<400> SEQUENCE: 49
catatggttc gtgca                                               15

<210> SEQ ID NO 50
<211> LENGTH: 31
<212> TYPE: DNA
<213> ORGANISM: Artificial
<220> FEATURE:
<223> OTHER INFORMATION: pT7CIIH6

```
<400> SEQUENCE: 50 gaaggggat cgcatcacca tcaccatcac g                              31

<210> SEQ ID NO 51
<211> LENGTH: 11
<212> TYPE: DNA
<213> ORGANISM: Artificial
<220> FEATURE:
<223> OTHER INFORMATION: pT7CIIH6

<400> SEQUENCE: 51
agcttgaatt c                                                   11

<210> SEQ ID NO 52
<211> LENGTH: 26
<212> TYPE: DNA
<213> ORGANISM: Artificial
<220> FEATURE:
<223> OTHER INFORMATION: TN123

<400> SEQUENCE: 52
gatccatcga gggtaggggc gagcca                                   26

<210> SEQ ID NO 53
<211> LENGTH: 8
<212> TYPE: DNA
<213> ORGANISM: Artificial
<220> FEATURE:
<223> OTHER INFORMATION: TN123

<400> SEQUENCE: 53 atcgtgta                                                        8

<210> SEQ ID NO 54
<211> LENGTH: 31
<212> TYPE: DNA
<213> ORGANISM: Artificial
<220> FEATURE:
<223> OTHER INFORMATION: pT7H6

<400> SEQUENCE: 54
catatgggat cgcatcacca tcaccatcac g                             31

<210> SEQ ID NO 55
<211> LENGTH: 11
<212> TYPE: DNA
<213> ORGANISM: Artificial
<220> FEATURE:
<223> OTHER INFORMATION: pT7H6

<400> SEQUENCE: 55
agcttgaatt c                                                   11

<210> SEQ ID NO 56
<211> LENGTH: 29
<212> TYPE: DNA
<213> ORGANISM: Artificial
<220> FEATURE:
<223> OTHER INFORMATION: TN12

<400> SEQUENCE: 56
gatccatcga gggtaggggc gagccacca                                29

<210> SEQ ID NO 57
<211> LENGTH: 11
<212> TYPE: DNA
```

```
<213> ORGANISM: Artificial
<220> FEATURE:
<223> OTHER INFORMATION: TN12

<400> SEQUENCE: 57
cagacggtct a                                                          11

<210> SEQ ID NO 58
<211> LENGTH: 29
<212> TYPE: DNA
<213> ORGANISM: Artificial
<220> FEATURE:
<223> OTHER INFORMATION: TN23

<400> SEQUENCE: 58
gatccatcca gggtagggtt gtgaacaca                                       29

<210> SEQ ID NO 59
<211> LENGTH: 11
<212> TYPE: DNA
<213> ORGANISM: Artificial
<220> FEATURE:
<223> OTHER INFORMATION: TN23

<400> SEQUENCE: 59
gggatcgtgt a                                                          11

<210> SEQ ID NO 60
<211> LENGTH: 26
<212> TYPE: DNA
<213> ORGANISM: Artificial
<220> FEATURE:
<223> OTHER INFORMATION: TN3

<400> SEQUENCE: 60
gatccatcga gggtagggcc ctgcag                                          26

<210> SEQ ID NO 61
<211> LENGTH: 11
<212> TYPE: DNA
<213> ORGANISM: Artificial
<220> FEATURE:
<223> OTHER INFORMATION: TN3

<400> SEQUENCE: 61
gggatcgtgt a                                                          11

<210> SEQ ID NO 62
<211> LENGTH: 31
<212> TYPE: DNA
<213> ORGANISM: Artificial
<220> FEATURE:
<223> OTHER INFORMATION: pT7H6

<400> SEQUENCE: 62
catatgggat cgcatcacca tcaccatcac g                                    31

<210> SEQ ID NO 63
<211> LENGTH: 11
<212> TYPE: DNA
<213> ORGANISM: Artificial
<220> FEATURE:
<223> OTHER INFORMATION: pT7H6

<400> SEQUENCE: 63
agcttgaatt c                                                          11
```

```
<210> SEQ ID NO 64
<211> LENGTH: 17
<212> TYPE: DNA
<213> ORGANISM: Artificial
<220> FEATURE:
<223> OTHER INFORMATION: UB

<400> SEQUENCE: 64
gatcacagat ctttgtg                                                     17

<210> SEQ ID NO 65
<211> LENGTH: 22
<212> TYPE: DNA
<213> ORGANISM: Artificial
<220> FEATURE:
<223> OTHER INFORMATION: UB

<400> SEQUENCE: 65
cgtggtggat cctaagcatg ca                                               22

<210> SEQ ID NO 66
<211> LENGTH: 6
<212> TYPE: DNA
<213> ORGANISM: Artificial
<220> FEATURE:
<223> OTHER INFORMATION: pT7H6

<400> SEQUENCE: 66 gaattc                                                                  6

<210> SEQ ID NO 67
<211> LENGTH: 17
<212> TYPE: DNA
<213> ORGANISM: Artificial
<220> FEATURE:
<223> OTHER INFORMATION: scFv(CEA6)

<400> SEQUENCE: 67
gatcccaggt tcagctg                                                     17

<210> SEQ ID NO 68
<211> LENGTH: 13
<212> TYPE: DNA
<213> ORGANISM: Artificial
<220> FEATURE:
<223> OTHER INFORMATION: scFv(CEA6)

<400> SEQUENCE: 68
ctgaatgggg ccg                                                         13

<210> SEQ ID NO 69
<211> LENGTH: 72
<212> TYPE: DNA
<213> ORGANISM: Artificial
<220> FEATURE:
<223> OTHER INFORMATION: pT7tribb

<400> SEQUENCE: 69
catatgggat cgcatcacca tcaccatcac ggatcaatcc agggaagatc tcctggtacc       60
gagccaccaa cc                                                          72

<210> SEQ ID NO 70
<211> LENGTH: 32
<212> TYPE: DNA
<213> ORGANISM: Artificial
<220> FEATURE:
```

<223> OTHER INFORMATION: pT7tripb

<400> SEQUENCE: 70
gccctgcaga cgggatccta aagcttgaat tc                32

<210> SEQ ID NO 71
<211> LENGTH: 52
<212> TYPE: PRT
<213> ORGANISM: Homo sapiens

<400> SEQUENCE: 71

Glu Pro Pro Thr Gln Lys Pro Lys Lys Ile Val Asn Ala Lys Lys Asp
 1               5                  10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys
    50

<210> SEQ ID NO 72
<211> LENGTH: 14
<212> TYPE: PRT
<213> ORGANISM: Artificial
<220> FEATURE:
<223> OTHER INFORMATION: tripa

<400> SEQUENCE: 72

Gly Ser Ile Gln Gly Arg Ser Pro Gly Thr Glu Pro Pro Thr
 1               5                  10

<210> SEQ ID NO 73
<211> LENGTH: 7
<212> TYPE: PRT
<213> ORGANISM: Artificial
<220> FEATURE:
<223> OTHER INFORMATION: tripa

<400> SEQUENCE: 73

Thr Val Ser Leu Lys Gly Ser
 1               5

<210> SEQ ID NO 74
<211> LENGTH: 14
<212> TYPE: PRT
<213> ORGANISM: Artificial
<220> FEATURE:
<223> OTHER INFORMATION: tripb

<400> SEQUENCE: 74

Gly Ser Ile Gln Gly Arg Ser Pro Gly Thr Glu Pro Pro Thr
 1               5                  10

<210> SEQ ID NO 75
<211> LENGTH: 6
<212> TYPE: PRT
<213> ORGANISM: Artificial
<220> FEATURE:
<223> OTHER INFORMATION: tripb

<400> SEQUENCE: 75

Ala Leu Gln Thr Gly Ser
 1               5

<210> SEQ ID NO 76

```
<211> LENGTH: 9
<212> TYPE: PRT
<213> ORGANISM: Artificial
<220> FEATURE:
<223> OTHER INFORMATION: pT7H6

<400> SEQUENCE: 76

Met Gly Ser His His His His His His
1               5

<210> SEQ ID NO 77
<211> LENGTH: 9
<212> TYPE: PRT
<213> ORGANISM: Artificial
<220> FEATURE:
<223> OTHER INFORMATION: pT7CIIH6

<400> SEQUENCE: 77

Gly Ser Ile Glu Gly Arg Gly Glu Pro
1               5

<210> SEQ ID NO 78
<211> LENGTH: 2
<212> TYPE: PRT
<213> ORGANISM: Artificial
<220> FEATURE:
<223> OTHER INFORMATION: pT7cIIH6

<400> SEQUENCE: 78

Ile Val
1

<210> SEQ ID NO 79
<211> LENGTH: 4
<212> TYPE: PRT
<213> ORGANISM: Artificial
<220> FEATURE:
<223> OTHER INFORMATION: pT7CIIH6

<400> SEQUENCE: 79

Met Val Arg Ala
1

<210> SEQ ID NO 80
<211> LENGTH: 10
<212> TYPE: PRT
<213> ORGANISM: Artificial
<220> FEATURE:
<223> OTHER INFORMATION: pT7CIIH6

<400> SEQUENCE: 80

Glu Gly Gly Ser His His His His His His
1               5                   10

<210> SEQ ID NO 81
<211> LENGTH: 9
<212> TYPE: PRT
<213> ORGANISM: Artificial
<220> FEATURE:
<223> OTHER INFORMATION: pT7CIIH6

<400> SEQUENCE: 81

Met Gly Ser His His His His His His
1               5

<210> SEQ ID NO 82
<211> LENGTH: 10
<212> TYPE: PRT
```

```
<213> ORGANISM: Artificial
<220> FEATURE:
<223> OTHER INFORMATION: pT7H6

<400> SEQUENCE: 82

Gly Ser Ile Glu Gly Arg Gly Glu Pro Pro
1               5                   10

<210> SEQ ID NO 83
<211> LENGTH: 3
<212> TYPE: PRT
<213> ORGANISM: Artificial
<220> FEATURE:
<223> OTHER INFORMATION: pT7H6

<400> SEQUENCE: 83

Gln Thr Val
1

<210> SEQ ID NO 84
<211> LENGTH: 10
<212> TYPE: PRT
<213> ORGANISM: Artificial
<220> FEATURE:
<223> OTHER INFORMATION: pT7H6

<400> SEQUENCE: 84

Gly Ser Ile Gln Gly Arg Val Val Asn Thr
1               5                   10

<210> SEQ ID NO 85
<211> LENGTH: 3
<212> TYPE: PRT
<213> ORGANISM: Artificial
<220> FEATURE:
<223> OTHER INFORMATION: pT7H6

<400> SEQUENCE: 85

Gly Ile Val
1

<210> SEQ ID NO 86
<211> LENGTH: 9
<212> TYPE: PRT
<213> ORGANISM: Artificial
<220> FEATURE:
<223> OTHER INFORMATION: pT7H6

<400> SEQUENCE: 86

Gly Ser Ile Glu Gly Arg Ala Leu Gln
1               5

<210> SEQ ID NO 87
<211> LENGTH: 9
<212> TYPE: PRT
<213> ORGANISM: Artificial
<220> FEATURE:
<223> OTHER INFORMATION: pT7H6

<400> SEQUENCE: 87

Met Gly Ser His His His His His
1               5

<210> SEQ ID NO 88
<211> LENGTH: 6
<212> TYPE: PRT
<213> ORGANISM: Artificial
<220> FEATURE:
```

<223> OTHER INFORMATION: pT7H6

<400> SEQUENCE: 88

Gly Ser Gln Ile Phe Val
1               5

<210> SEQ ID NO 89
<211> LENGTH: 4
<212> TYPE: PRT
<213> ORGANISM: Artificial
<220> FEATURE:
<223> OTHER INFORMATION: pT7H6

<400> SEQUENCE: 89

Arg Gly Gly Ser
1

<210> SEQ ID NO 90
<211> LENGTH: 14
<212> TYPE: PRT
<213> ORGANISM: Artificial
<220> FEATURE:
<223> OTHER INFORMATION: pT7H6

<400> SEQUENCE: 90

Gly Ser Ile Gln Gly Arg Ser Pro Gly Thr Glu Pro Pro Thr
1               5                   10

<210> SEQ ID NO 91
<211> LENGTH: 6
<212> TYPE: PRT
<213> ORGANISM: Artificial
<220> FEATURE:
<223> OTHER INFORMATION: pT7H6

<400> SEQUENCE: 91

Ala Leu Gln Thr Gly Ser
1               5

<210> SEQ ID NO 92
<211> LENGTH: 28
<212> TYPE: DNA
<213> ORGANISM: Artificial
<220> FEATURE:
<223> OTHER INFORMATION: pT7H6

<400> SEQUENCE: 92
gccctgcaga cgggatccta ataagctt                                    28

<210> SEQ ID NO 93
<211> LENGTH: 9
<212> TYPE: PRT
<213> ORGANISM: Artificial
<220> FEATURE:
<223> OTHER INFORMATION: pT7H6

<400> SEQUENCE: 93

Met Gly Ser His His His His His His
1               5

<210> SEQ ID NO 94
<211> LENGTH: 5
<212> TYPE: PRT
<213> ORGANISM: Artificial
<220> FEATURE:
<223> OTHER INFORMATION: pT7tripb

<400> SEQUENCE: 94

Ser Gln Val Gln Leu
1               5

<210> SEQ ID NO 95
<211> LENGTH: 4
<212> TYPE: PRT
<213> ORGANISM: Artificial
<220> FEATURE:
<223> OTHER INFORMATION: pT7tripb

<400> SEQUENCE: 95

Leu Asn Gly Ala
1

<210> SEQ ID NO 96
<211> LENGTH: 23
<212> TYPE: PRT
<213> ORGANISM: Artificial
<220> FEATURE:
<223> OTHER INFORMATION: pT7tripb

<400> SEQUENCE: 96

Met Gly Ser His His His His His His Gly Ser Ile Gln Gly Arg Ser
1               5                   10                  15

Pro Gly Thr Glu Pro Pro Thr
            20

<210> SEQ ID NO 97
<211> LENGTH: 6
<212> TYPE: PRT
<213> ORGANISM: Artificial
<220> FEATURE:
<223> OTHER INFORMATION: pT7tripb

<400> SEQUENCE: 97

Ala Leu Gln Thr Gly Ser
1               5

<210> SEQ ID NO 98
<211> LENGTH: 5
<212> TYPE: PRT
<213> ORGANISM: Artificial
<220> FEATURE:
<223> OTHER INFORMATION: pT7tripb

<400> SEQUENCE: 98

Ser Gln Val Gln Leu
1               5

<210> SEQ ID NO 99
<211> LENGTH: 4
<212> TYPE: PRT
<213> ORGANISM: Artificial
<220> FEATURE:
<223> OTHER INFORMATION: pT7tripb

<400> SEQUENCE: 99

Leu Asn Gly Ala
1

<210> SEQ ID NO 100
<211> LENGTH: 14
<212> TYPE: DNA
<213> ORGANISM: Artificial
<220> FEATURE:
<223> OTHER INFORMATION: pT7tripb

```
<400> SEQUENCE: 100
ctgaatgggg ccta                                                    14

<210> SEQ ID NO 101
<211> LENGTH: 23
<212> TYPE: PRT
<213> ORGANISM: Artificial
<220> FEATURE:
<223> OTHER INFORMATION: pT7tripb

<400> SEQUENCE: 101

Met Gly Ser His His His His His His Gly Ser Ile Gln Gly Arg Ser
1               5                   10                  15

Pro Gly Thr Glu Pro Pro Thr
            20

<210> SEQ ID NO 102
<211> LENGTH: 6
<212> TYPE: PRT
<213> ORGANISM: Artificial
<220> FEATURE:
<223> OTHER INFORMATION: pT7tripb

<400> SEQUENCE: 102

Ala Leu Gln Thr Gly Ser
1               5

<210> SEQ ID NO 103
<211> LENGTH: 4
<212> TYPE: PRT
<213> ORGANISM: Artificial Sequence
<220> FEATURE:
<223> OTHER INFORMATION: FXa Cleavage site

<400> SEQUENCE: 103

Ile Gln Gly Arg
1

<210> SEQ ID NO 104
<211> LENGTH: 4
<212> TYPE: PRT
<213> ORGANISM: Artificial Sequence
<220> FEATURE:
<223> OTHER INFORMATION: FXa protease site

<400> SEQUENCE: 104

Ile Glu Gly Arg
1
```

TRIMERISING MODULE

This application is a continuation of U.S. application Ser. No. 11/452,434, filed on Jun. 14, 2006, which is a continuation of U.S. application Ser. No. 09/445,576, filed on Jul. 17, 2000, which is a national stage application under 35 U.S.C. §371 of International Application No. PCT/DK98/00245, filed on Jun. 11, 1998, which claims the benefit of Denmark Application No. DK0685/97, filed on Jun. 11, 1997, the disclosures of which are explicitly incorporated by reference herein.

The present invention relates to the design of trimeric polypeptides using polypeptide structural elements derived from the tetranectin protein family, and their use in rational de novo design and production of multi-functional molecules including the application of the multi-functional molecules in protein library technology, such as phage display technology, diagnostic and therapeutic systems, such as human gene therapy and imaging.

BACKGROUND OF THE INVENTION

Tetranectin is a $Ca^{2+}$-binding trimeric C-type lectin which is present in blood plasma and from the extracellular matrix of certain tissues. The tetranectin group of proteins comprises tetranectin isolated from man and from mouse and the highly related C-type lectin homologues isolated from the cartilage of cattle (Neame and Boynton, database accession number PATCHX:u22298) and from reef shark (Neame et al., 1992, Neame et al., 1996 and database accession number p26258 and PIR2:A37289).

The mature tetranectin polypeptide chain of 181 amino acid residues is encoded in three exons as shown by molecular cloning and characterisation of the gene (Berglund & Petersen, 1992; Wewer & Albrechtsen, 1992). Exon 3 of the human tetranectin gene encodes a separate functional and structural unit, a single long-form so-called carbohydrate recognition domain (CRD), with three intra-chain disulphide bridges. The tetranectin CRD is considered to belong to a distinct class of C-type lectins (Day, 1994) clearly related to C-type lectins by sequence homology, conservation of disulphide topology (Fuhlendorff et al, 1987) and by the presence of an almost conserved suit of amino acid residues known to be involved in binding of calcium ions.

A published poster (Holtet et al 1996) has proposed tetranectin to be a trimer and that trimerisation is governed by the peptide encoded by exon 1. The peptide encoded by exon 1 was proposed to be "necessary and sufficient to govern trimerisation" whereas the polypeptide encoded by exon 2 was proposed as being "involved in lysine-sensitive binding to plasminogen".

Tetranectin was first identified as a plasma protein binding to plasminogen by binding to the kringle-4 domain of plasminogen. Recent unpublished results (Graversen et al., manuscript for PNAS) proves (1) that the site in tetranectin involved in binding to plasminogen resides entirely in the CRD-domain (encoded by exon 3), (2) that binding is calcium sensitive, and (3) that the kringle-4 binding site in tetranectin overlaps the putative carbohydrate binding site of the CRD domain. Hence, there is now surprising definitive evidence that TN exons 1 and 2, i.e. the trimerisation unit in TN does not exhibit any plasminogen-binding affinity. Accordingly, an artificial protein containing a TTSE unit as part of its architecture is not expected to interact with plasminogen or plasmin due to properties inherited from tetranectin.

Tetranectin has also been reported to bind to sulfated polysaccharides like heparin (Clemmensen (1989) Scand J. Clin. Lab. Invest. vol 49:719-725). We have new results showing that the CRD domains of tetranectin are not involved in this protein-polysaccharide interaction. In fact, the site in tetranectin is located in the N-terminal region of exon 1 and may be abolished by removal or mutagenis of N-terminal lysine residues (Graversen et al., manuscript), processes that do not inhibit trimerisation. TTSEs that include most or all of TN exon 1 therefore confer an affinity for sulfated polysaccharides to any designed protein which encompasses such a TTSE as part of its structure. If desired, however, this affinity can be reduced or abolished by N-terminal truncation or mutagenesis of lysine residues in the part of the TTSE that corresponds to the N-terminal 8-10 amino acid residues of exon 1 (Graversen et al., unpublished).

With respect to gene therapy which is also within the scope of the present invention, there is only a limited number of basic strategies for gene therapy which show some promise in preclinical models so far. The two major strategies e.g for the treatment of malignant tumors are cytokine-gene aided tumor vaccination and selective prodrug activation. Whereas the first strategy relies on the strong immunostimulatory effect of a relatively small number of genetically modified cytotoxic T cells or tumor cells, the second one is based on conversion of a nontoxic prodrug into a toxic product by an enzyme-encoding gene where the toxic effect is exerted also on non-transduced dividing tumor cells due to a so-called bystander effect. Alternatively, strategies can be envisaged where the malignant phenotype of a cell is reversed by either inactivating an oncogene or reestablishing an inactivated tumor suppressor gene. In both cases, highly efficient gene transfer to the cells in a tumor is required. Although high efficiencies of gene transfer can be obtained in vitro and even in vivo under certain circumstances, correction of the malignant phenotype by reversing the major oncogenic change in the tumor cells is unlikely to result in normal cells. Thus, selective induction of tumor cell death by use of the present invention would be preferable, and the development of methods enabling such induction will be of great importance.

A major problem in connection with the gene therapy is the incorporation of foreign material into the genome. Viruses, however, have only been partially successful in overcoming this problem. Hence the initial efforts at gene therapy are still directed towards engineering viruses so that they could be used as vectors to carry therapeutic genes into patients. In the still very immature in vivo method of somatic gene therapy, where a vector could be injected directly into the bloodstream, or more preferably by transmucosal delivery, the present invention may be utilized due to the surprising number of ways the gene therapy may be targeted.

For many gene-therapy applications in the future, it is probable that a synthetic hybrid system will be used that incorporates engineered viral component for target-specific binding and core entry, immunosuppressive genes from various viruses and some mechanism that allows site-specific integration, perhaps utilizing AAV sequences or an engineered retroviral integrase protein. In addition, regulatory sequences from the target cell itself will be utilized to allow physiological control of expression of the inserted genes. All these components would be assembled in vitro in a liposome-like formulation with additional measures taken to reduce immunogenicity such as concealment by PEG As mentioned, one of the current problems in gene therapy is the efficient delivery of nucleic acids to as many as possible of a specific population of cells in the body, and it is often not possible to find e.g. an appropriate viral vector that will find that particular cell population efficiently and selectively (Review on aspects of gene therapy: Schaper, W & Ito, W. D.

Current Opinion in Biotechnology, 1996, vol. 7, 635-640. Nature Biotechnology 1998 vol 16 is an entire volume dedicated to protein- and gene delivery).

Given the possibility of in vitro generation of a human antibody against virtually any target antigen by phage technology, it follows that TTSES, where one of the subunits is modified with a membrane integrating or associating entity, may be used as a practicable tool for generating a viral, bacterial or preferentially artificially assembled lipomal vehicle that will allow selective delivery of the contained material by infection or transfection of any cell population to which such a specific antibody may be generated. Moreover vehicles may, with the use of TTSEs, be individualised by selection of patient specific antibodies or by assembling TTSE units conjugated with scFvs selected from an ensemble of antibodies selected by the particular markers of the disease.

SUMMARY OF THE INVENTION

It has surprisingly been found by the present inventors that the human tetranectin polypeptide (and derivatives thereof) is capable of forming very stable trimers which have a number of advantageous characteristics and uses. Notably, the tetranectin molecule includes a trimerising structural element which can be used as carrier of other chemical entities, thereby providing a carrier molecule of a hitherto unseen versatility.

Prior published knowledge in the field of providing trimerising polypeptides of choice includes the disclosure in WO 95/31540 by Hoppe and Reid which describes a trimerisation module derived from collectin coiled coil structures and its application in engineering of artificially trimerised proteins. Several interesting areas of application are common to that patent publication and to the present disclosure. However, in several ways the properties of the trimerisation modules derived from the tetranectin protein family as disclosed herein are markedly different in fundamental architecture and represent surprisingly improved properties in comparison with the collectin trimerisation unit:

(1) Although the spatial structures of both trimerisation modules at a superficial level appear as similar in that both are ternary coiled coil structures of roughly equivalent spatial size the structural basis for adopting this spatial configuration is markedly distinct between the two groups of proteins. In fact, it is so distinct that the common belief prior to the work of Holtet et al. on cross-linking of human tetranectin (Holtet et al., 1996) was that this family of proteins were tetrameric (hence the name). Accordingly, the sequences of the tetranectin family of trimerisation modules does not conform to the declared common motif delineated for the collectin family (WO 95/31540, page 8).

(2) The thermal stability of the tetranectin trimerisation module (as shown in the examples) is such that the trimer can be shown to exist even at about 60° C. (Example 4, trimerised tetranectin) or at about 70° C. (Example 3, trimerised ubiquitin), whereas a collectin trimer unit falls apart at about 50-55° C. (WO 95/31540, Example 1, page 36 therein).

(3) Whereas it remains uncertain whether the collectin trimerisation domain possibly allows attachment of fusion partners at C-terminal ends of the trimerisation module, and whereas no example has been reported of successful or claimed successful attachment of a foreign protein (except for the GST fusion partner) to the N-terminal region of the collectin trimerisation module, the information disclosed herein demonstrates that the tetranectin trimerisation module is more versatile in that is allows attachment of foreign proteins to either, as well as to both, terminus or termini simultaneously (Examples 1-4). This has important consequences as the tetranectin trimerisation module may be deployed to construct molecules that are able to interact (each end with a binding valency up to 3) simultaneously with two bulky interaction partners like e.g. cell surfaces.

(4) The virtual absence of subunit exchange between monomers of a trimer that has been trimerised using the tetranectin trimerisation modules disclosed herein is by first principles of thermodynamics correlated with the surprisingly high thermal stability of the complex. It will hence be apparent that the advantages inherent to the "pick-and-mix" applications of the technology, as disclosed herein, may be used to much greater advantage because of the much longer shelf life expected for the heterofunctional products of the present invention.

The polypeptide constructs CIIH6FXTN123, H6FXTN123, H6FXTN12, and H6FXTN23 which all involve parts of the tetranectin molecule have previously been prepared (cf. e.g. WO 94/18227) but these constructs have all been provided with a view to facilitating expression and/or purification of the tetranectin derived moiety of the constructs. To the best of the inventors' knowledge no publications exist which reports any use of tetranectin derivatives as "building blocks" to which other chemical moieties advantageously could be coupled.

Hence, in its broadest aspect the present invention relates to a monomer polypeptide construct comprising at least one tetranectin trimerising structural element (hereinafter designated a TTSE) which is covalently linked to at least one heterologous moiety, said TTSE being capable of forming a stable complex with two other TTSEs, with the proviso that the heterologous moiety is different from any of the fusion proteins CIIH6FXTN123, H6FXTN123, H6FXTN12, H6FXTN23, the sequences of which are shown in SEQ ID NOs: 24-27. It is preferred that the heterologous moiety is one which does not exclusively facilitate expression and/or purification of the monomer polypeptide construct.

The invention further relates to oligomeric molecules comprised of at least two of such monomer polypeptide constructs, and the invention also relates to methods of preparing the monomer polypeptide constructs and the oligomers. The invention further relates to a kit comprising monomer polypeptide constructs in separate packages, ready for use in a "pick-and-mix" approach for use of the monomers. This pick and mix approach is for use in therapeutic as well as for dianostic use. Eg. having a tumor with a known and specific epitope to which an antibody is available. The kit may then comprise a first TTSE conjugated to an relevant antibody, a second component which may comprise af TTSE coupled to an imaging compound. In a second aspect the second component may comprise a drug or a prodrug relevant for treating the tumor. In a still further aspect a third TTSE component being a monitoring compound, e.g. indicative of the progress of the targeting.

As is clear from this illustration the present invention relates to a large amount of combinations allowing an individual design for a large number of circumstances.

Finally, the invention also pertains to fragments which include nucleic acid sequences which encode the monomer polypeptide constructs, as well as to vectors and cells containing these nucleic acid fragments.

LEGENDS TO THE FIGURES

FIG. 1: Amino acid sequence of the amino terminal region of tetranectin.

Amino acid sequence (in one letter code) from E1 to L51 of tetranectin (SEQ ID NO: 7). Exon 1 comprises residues E1 to D16 and exon 2 residues V17 to V49, respectively. The alpha helix extends beyond L51 to K52 which is the C-terminal amino acid residue in the alpha helix.

FIG. 2: Alignment of the amino acid sequences of the trimerising structural element of the tetranectin protein family.

Amino acid sequences (one letter code) corresponding to residue V17 to K52 comprising exon 2 and the first three residues of exon 3 of human tetranectin (SEQ ID NO: 7); murine tetranectin (Sørensen et al., Gene, 152: 243-245, 1995); tetranectin homologous protein isolated from reef-shark cartilage (Neame and Boynton, 1992, 1996); and tetranectin homologous protein isolated from bovine cartilage (Neame and Boynton, database accession number PATCHX: u22298). Residues at a and d positions in the heptad repeats are listed in boldface. The listed consensus sequence of the tetranectin protein family trimerising structural element comprise the residues present at a and d positions in the heptad repeats shown in the figure in addition to the other conserved residues of the region. "hy" denotes an aliphatic hydrophobic residue.

Figure 3:
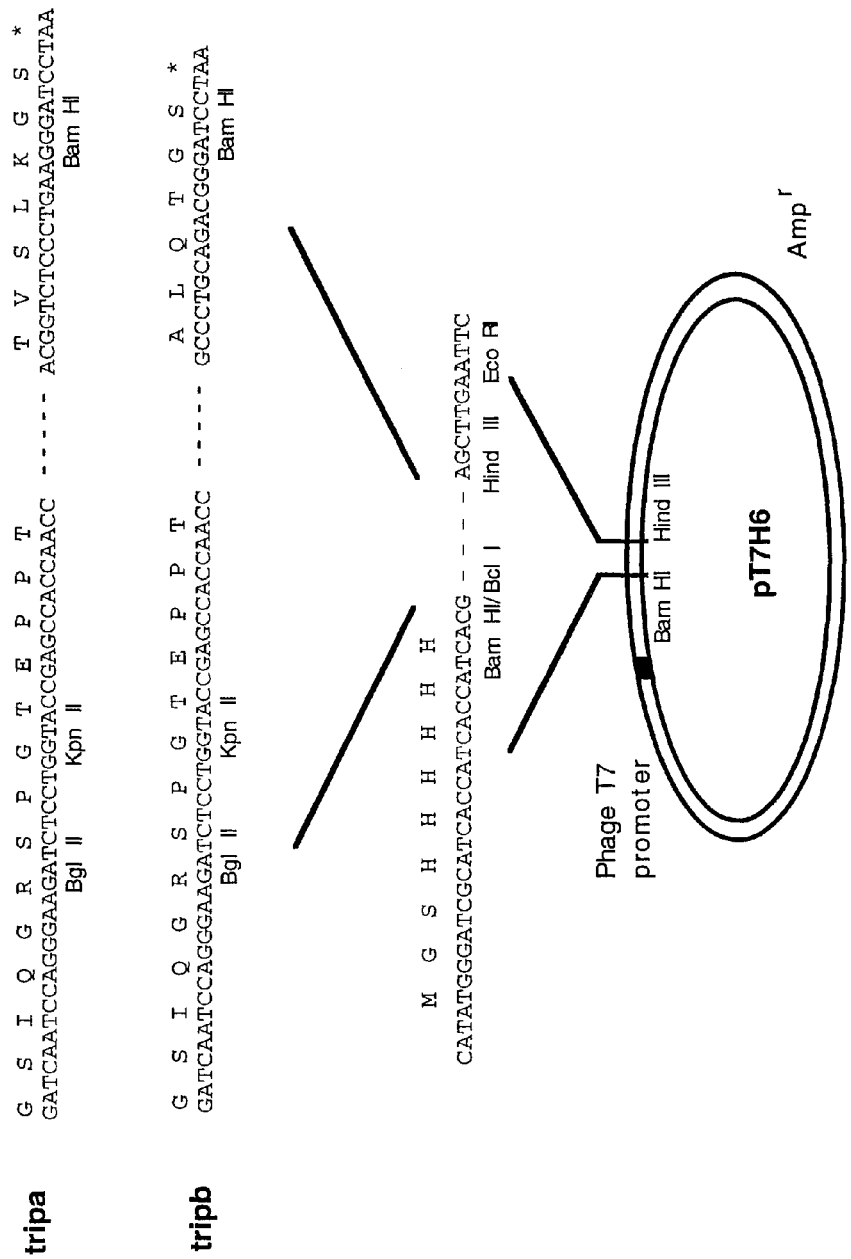

FIG. 3: Construction of the expression plasmids pTH6FXtripa and pTH6FXtripb.

The amplified DNA fragments tripa and tripb harbouring the tetranectin amino acid sequence (SEQ ID NO: 7) from E1 to T48 and E1 to K52, respectively, fused in the 5' end to nucleotide sequences encoding a $FX_a$ cleavage site IQGR (SEQ ID NO: 4) and the recognition sites for the restriction endonucleases BglII and KpnI, were cut with the restriction enzymes BclI and HindIII and ligated into the BamHI and HindIII sites of the expression plasmid pT7H6 (Christensen et al., 1991) using standard procedures.

FIG. 4: Predicted amino acid sequence of the fusion proteins H6FXtripa (SEQ ID NO: 28) and H6FXtripb (SEQ ID NO: 29) encoded by the expression plasmids pTH6FXtripa and pTH6FXtripb, respectively.

FIG. 5: Construction of the expression plasmids pTH6FXTN123 and pTCIIH6FXTN123.

The amplified DNA fragment corresponding to the full length, mature tetranectin monomer (SEQ ID NO: 7) from E1 to V181 fused in the 5' end to nucleotide sequences encoding a $FX_a$ cleavage site IEGR (SEQ ID NO: 10) was cut with the restriction enzymes BamHI and HindIII and ligated into the corresponding sites of the expression plasmids pT7H6 (Christensen et al., 1991) and pTCIIH6 using standard procedures. pTCIIH6 was derived from pT7H6 by substitution of the NdeI-HindIII fragment of pT7H6 with the NdeI-HindIII fragment of pLcII (Nagai and Thøgersen, 1987) encoding the first 32 residues of the lambda cII protein MVRANKRNEALRIESALLNKIAMLGTEKTAEG (SEQ ID NO: 11) fused in the 3' end to a nucleotide sequence encoding the H6 sequence GSHHHHHHGS (SEQ ID NO: 12).

FIG. 6: Predicted amino acid sequence of the fusion proteins H6FXTN123 (SEQ ID NO: 25) and CIIH6FXTN123 (SEQ ID NO: 24) encoded by the expression plasmids pTH6FXTN123 and pTCIIH6FXTN123, respectively.

Figure 7:
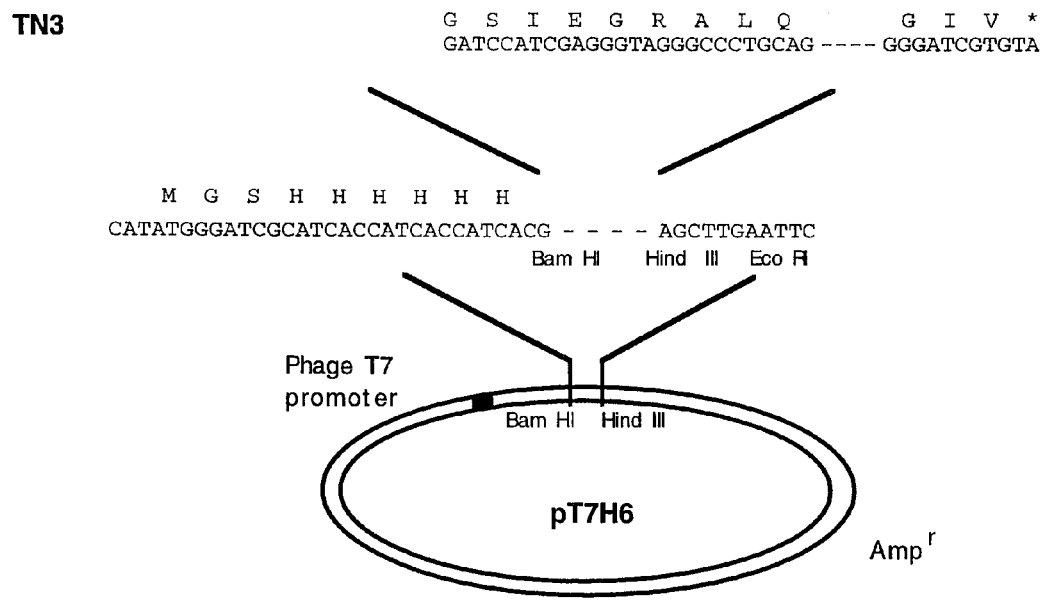

FIG. 7: Construction of the expression plasmids pTH6FXTN12, pTH6FXTN23, and pTH6FXTN3.

The amplified DNA fragments corresponding to the tetranectin derivatives TN12 and TN3 from E1 to V49 and A45 to V181, respectively (SEQ ID NO: 7) fused in the 5' end to nucleotide sequences encoding the $FX_a$ cleavage site IEGR (SEQ ID NO: 10) was cut with the restriction enzymes BamHI and HindIII and ligated into the corresponding sites of the expression plasmids pT7H6 (Christensen et al., 1991) using standard procedures. The amplified DNA fragment corresponding to the tetranectin derivative TN23 from V17 to V181 (SEQ ID NO: 7) fused in the 5' end to nucleotide sequences encoding the $FX_a$ cleavage site IQGR (SEQ ID NO: 4) was cut with the restriction enzymes BamHI and HindIII and ligated into the corresponding sites of the expression plasmids pT7H6 (Christensen et al., 1991) using standard procedures.

FIG. 8: Predicted amino acid sequence of the fusion proteins H6FXTN12 (SEQ ID NO: 26), H6FXTN23 (SEQ ID NO: 27), and H6FXTN3 (SEQ ID NO: 30) encoded by the expression plasmids pTH6FXTN12, pTH6FXTN12, respectively.

Figure 9:
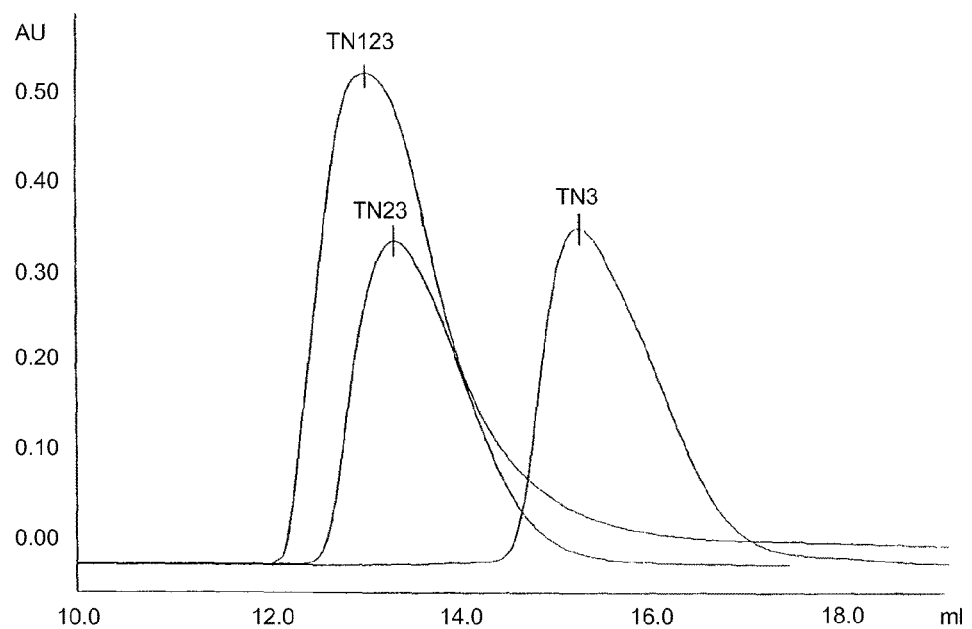

FIG. 9: Gel filtration analysis of TN123, TN23, and TN3

Analytical gel filtration of the recombinant tetranectin derivatives TN123, TN23, and TN3 were performed on a Superose 12 HR 10/30 column (Pharmacia, Sweden) with a total volume of 25 ml in 100 mM NaCl and 50 mM Tris-HCl pH 8 and a flow rate of 0.2 ml/min. Vertical bars at peak maxima identify elution profiles for each of the three proteins.

Figure 10:
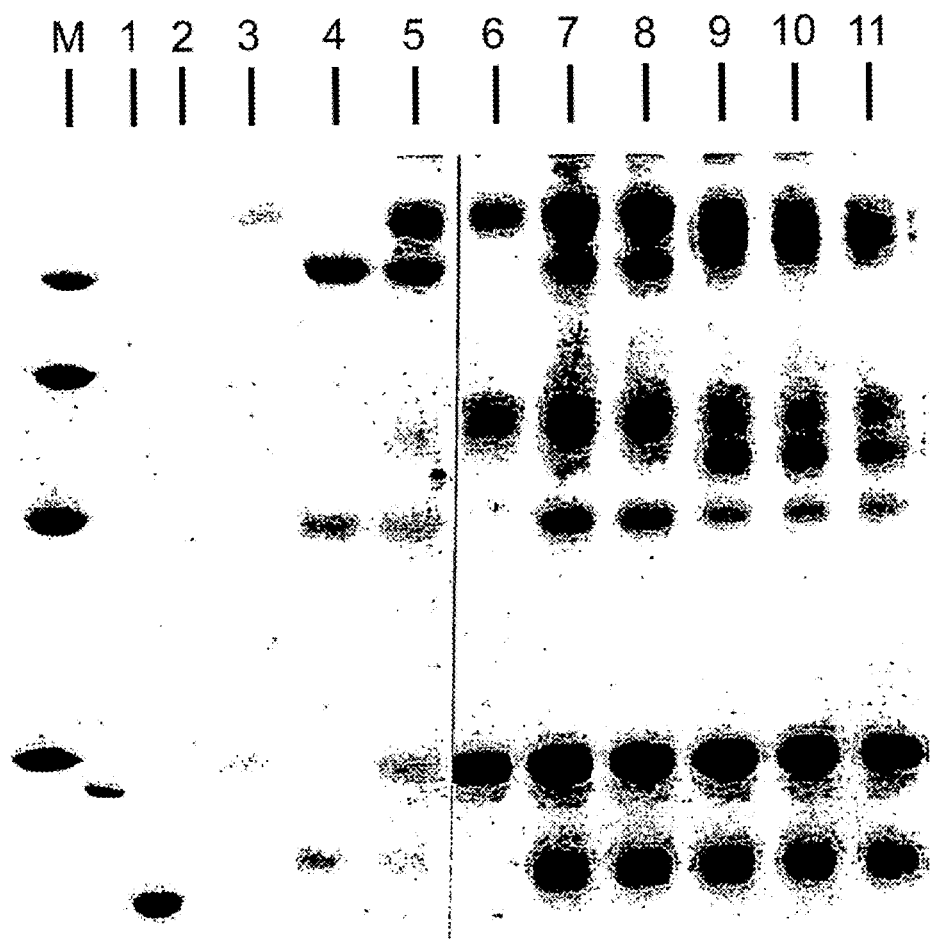

FIG. 10: Cross-linking analysis of TN123 and CIIH6FXTN123.

Samples of TN123, CIIH6FXTN123 and mixtures of both were incubated with DMSI and analyzed by SDS-PAGE (12% gel). p Before addition of DMSI, protein mixtures were subjected to subunit exchange by incubation at 70° C. for varying length of time. Protein marker of 94, 68, 43 and 30 kDa, top to bottom (lane M). CIIH6FXTN123 fusion protein (lane 1). TN123 (lane 2). DMSI treated CIIH6FXTN123 (lanes 3 and 6). DMSI-treated TN123 (lane 4). Identical samples of DMSI treated mixtures of CIIH6FXTN123 and TN123 without heat exposure (lanes 5 and 7) and heat treated for 2.5 sec, 15 sec, 2.5 min. and 10 min., respectively, before treatment with DMSI (lanes 8-11).

Figure 11:
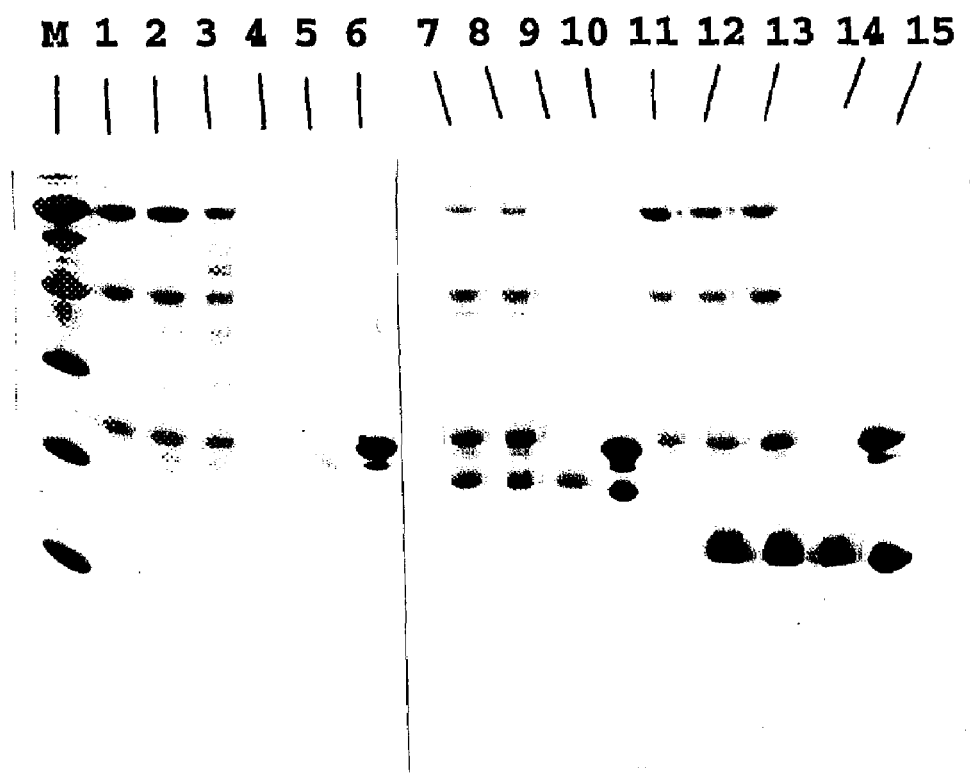

FIG. 11: Cross-linking analysis of the recombinant tetranectin derivatives TN123, TN23, TN3, and H6FXTN12.

The recombinant proteins TN123, TN23, TN3, H6FXTN12 or mixtures of TN123 and each of the other were analyzed by SDS-PAGE. Protein marker of 94, 68, 43, 30, 20, and 14.4 kDa, top to bottom (lane M). TN123 cross-linked with DMSI (lane 1). TN123 and H6-rTN12 cross-linked with DMSI without and with heat treatment at 70° C. for two min. (lanes 2 and 3). H6FXTN12 cross-linked with DMSI (lanes 4 and 5). Mixture of TN123 and H6FXTN12, no cross-linking (lane 6). Cross-linking of TN123 and TN23 without and with heat treatment at 70° C. for two min. (lanes 7 and 8). Cross-linking of TN23 (lane 9). Mixture of TN123 and TN23 without cross-linking (lane 10). TN123 cross-linked by DMSI (lane 11). Cross-linking of TN123 and TN3 without and with heat treatment for two min. (lanes 12 and 13). Cross-linking of TN3 (Lane 14). Mixture of TN123 and TN3, no cross-linking (lane 15).

Figure 12:

FIG. 12: Cross-linking based analysis of the trimer thermal stability.

In parallel experiments TN123 and the fusion protein H6FXtripb-UB (SEQ ID NO: 31) were cross-linked with DMSI at different temperatures and the samples analyzed by SDS-PAGE. Protein marker of 94, 68, 43, 30, 20, and 14.4 kDa, top to bottom (lane M). TN123 without cross-linking (lane 1). TN123 cross-linked with DMSI for 15 min. at 37° C., 50° C., 60° C., and 70° C. (lanes 2 to 5), respectively. The fusion protein H6FXtripb-UB (SEQ ID NO: 31) without cross-linking (lane 6). H6FXtripb-UB cross-linked with DMSI for 15 min. at 37° C., 50° C., 60° C., and 70° C. (lanes 7 to 10), respectively and H6FXtripb-UB incubated at 70° C. for 15 min. (lane 11).

Figure 13:
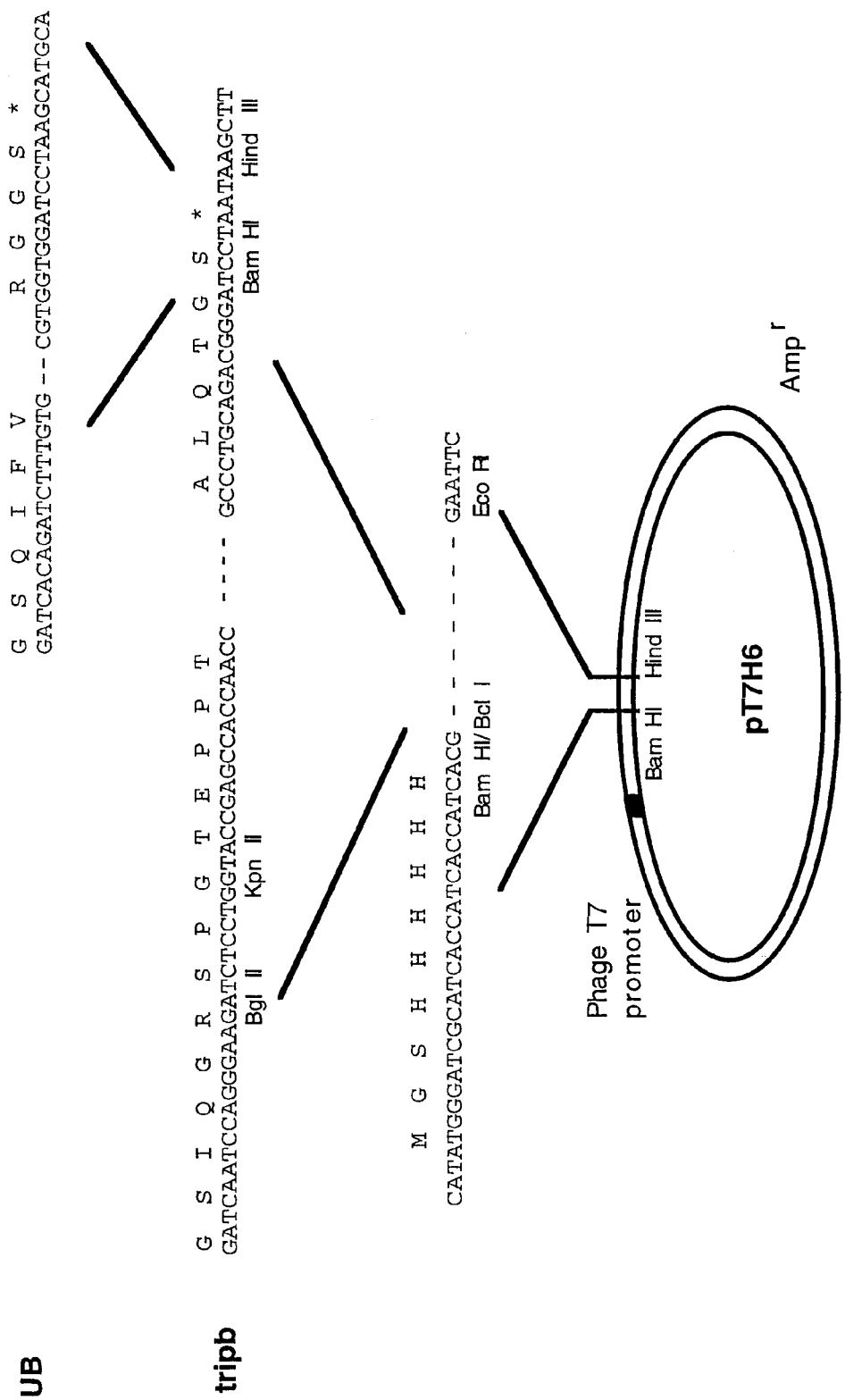

FIG. 13: Construction of the expression plasmid pTH6FXtripb-UB.

The amplified DNA fragment comprising the nucleotide sequence (SEQ ID NO:16) encoding the ubiquitin amino acid sequence (SEQ ID NO: 19) from Q2 to G76 was cut with the restriction enzymes BclI and HindIII and ligated into the BamHI and HindIII sites of the expression plasmid pT7H6FXtripb (Example 1) using standard procedures.

FIG. 14: Predicted amino acid sequence of the fusion protein H6FXtripb-UB (SEQ ID NO: 31) encoded by the expression plasmid pTH6FXtripb-UB.

Figure 15:
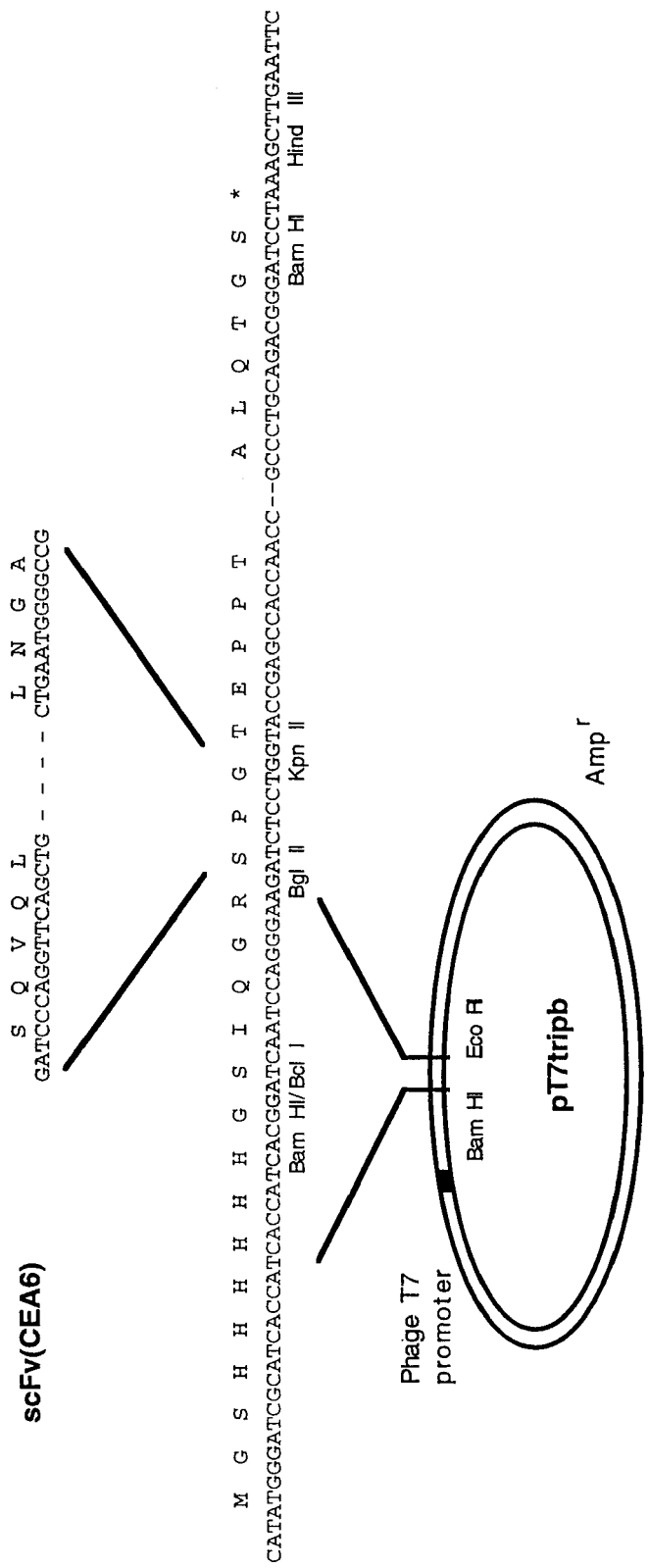

FIG. 15: Construction of the expression plasmid pTH6FXscFV(CEA6)tripb.

The DNA fragment, amplified with the primer pair SEQ ID NOs: 21 and 22, comprising the nucleotide sequence SEQ ID NO: 20 encoding the single chain antibody CEA6, scFV (CEA6), amino acid sequence from Q1 to A261 was cut with the restriction enzymes BamHI and KpnI and ligated into the BglII and KpnI sites of the expression plasmid pT7H6FXtripb (Example 1) using standard procedures.

FIG. 16: Predicted amino acid sequence of the fusion protein HGFXscFV(CEA6)tripb encoded by the expression plasmid pH6FXscFV(CEA6)tripb.

Figure 17:
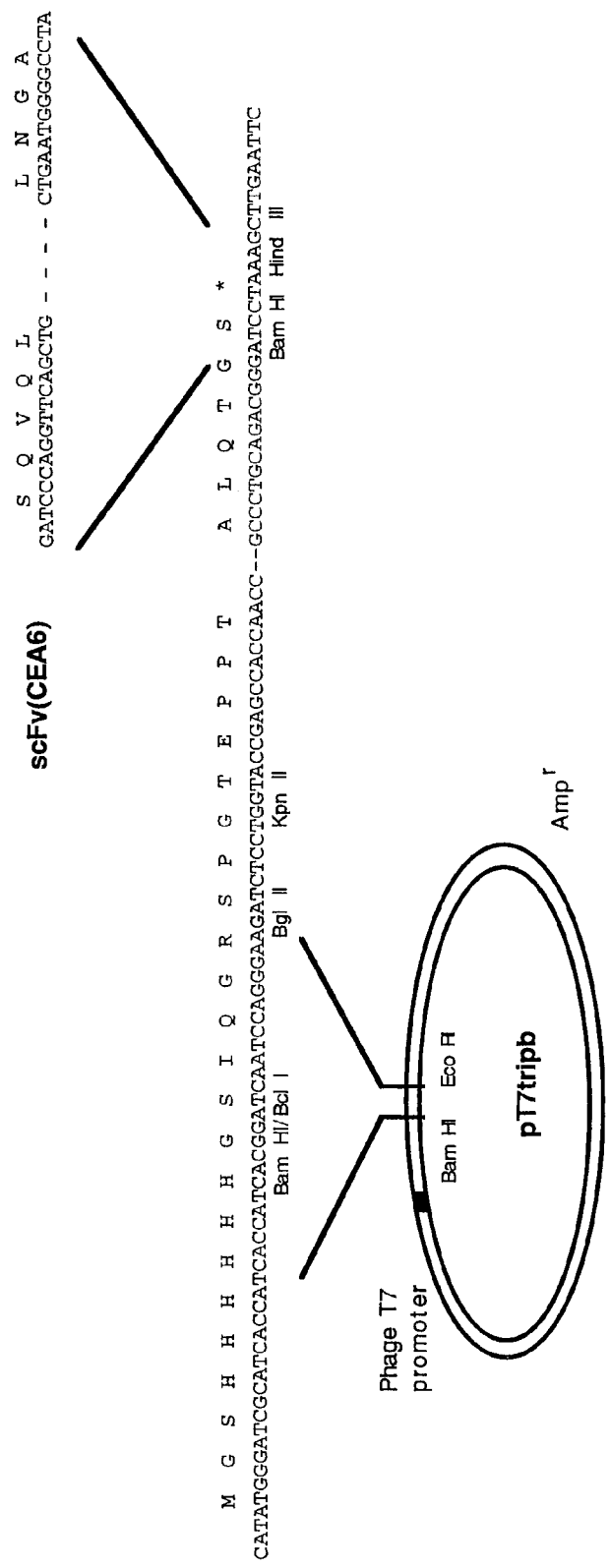

FIG. 17: Construction of the expression plasmid pTH6FXtripbscFX(CEA6).

The DNA fragment, amplified with the primer pairs having SEQ ID NO: 21 and 23, comprising the nucleotide sequence (SEQ ID NO: 20) encoding the single chain antibody CEA6, scFV (CEA6), amino acid sequence from Q1 to A261 was cut with the restriction enzymes BamHI and HindIII and ligated into the BamHI and HindIII sites of the expression plasmid pT7H6FXtripb (Example 1) using standard procedures.

FIG. 18: Predicted amino acid sequence of the fusion protein H6FXtripbscFv(CEA6) encoded by the expression plasmid pH6FXtripbscFv(CEA6).

Figure 19:
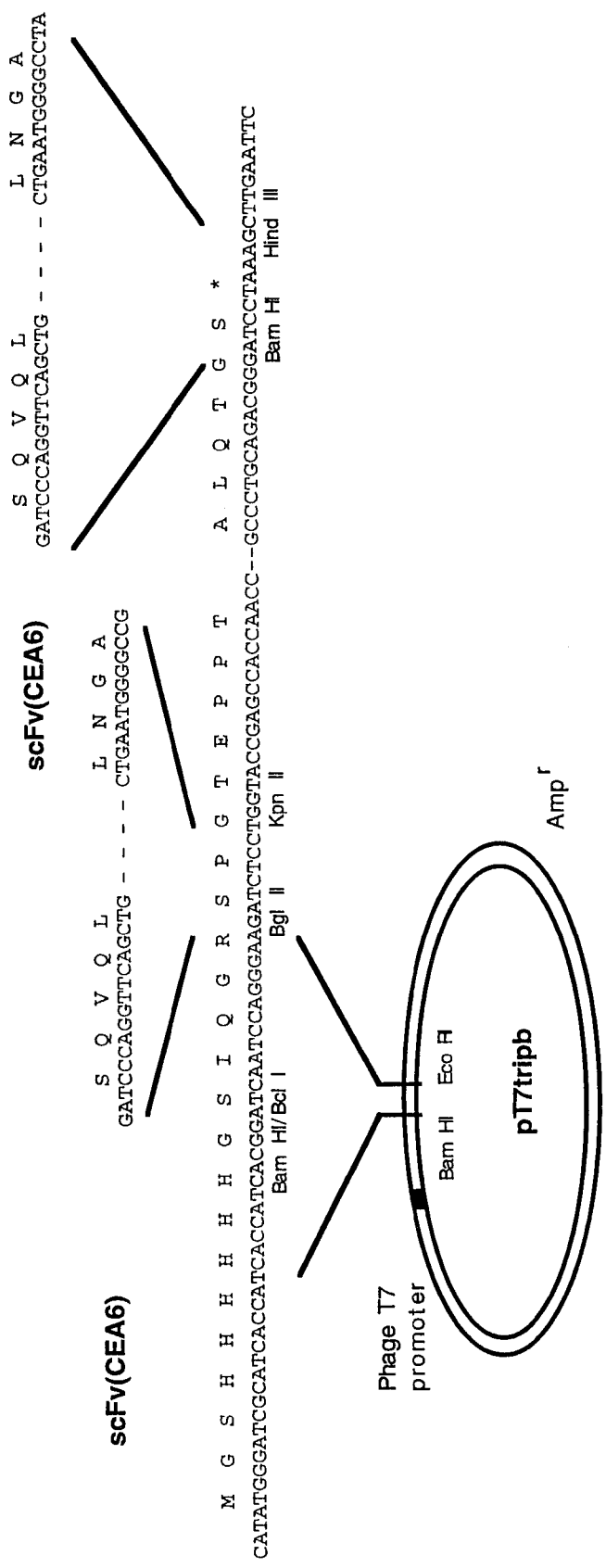

FIG. 19: Construction of the expression plasmid pTH6FXscFv(CEA6)tripbscFX(CEA6).

The DNA fragment, amplified with the primer pair SEQ ID NO: 21 and 23, comprising the nucleotide sequence (SEQ ID NO: 20) encoding the single chain antibody CEA6, scFV (CEA6), amino acid sequence from Q1 to A261 was cut with the restriction enzymes BamHI and HindIII and ligated into the BamHI and HindIII sites of the expression plasmid pT7H6FXscFv(CEA6)tripb (Example 4) using standard procedures.

FIG. 20: Predicted amino acid sequence of the fusion protein H6FXscFv(CEA6)tripbscFv(CEA6) (SEQ ID NO: 34) encoded by the expression plasmid pH6FXscFv(CEA6)tripbscFv(CEA6).

Figure 21:
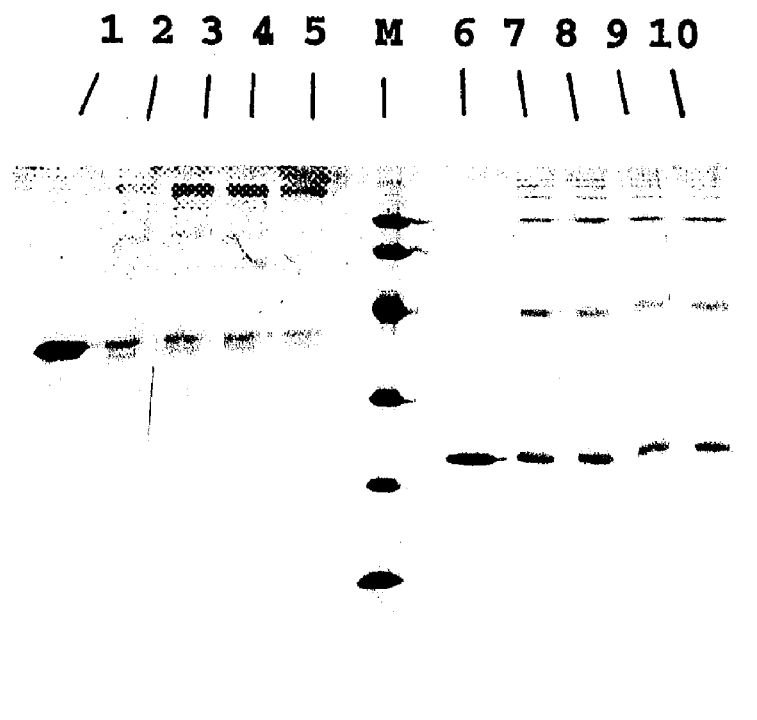

FIG. 21: Cross-linking analysis of the H6FXtripbscFv (CEA6) fusion protein (SEQ ID NO: 33).

In parallel experiments the fusion proteins H6FXtripbscFv (CEA6) (SEQ ID NO: 33) and TN123 were cross-linked at room temperature for 30 min. with 0 mg/ml, 0.5 mg/ml, 1.0 mg/ml, 1.5 mg/ml, and 2.0 mg/ml of DMSI, respectively. Lane 1: H6FXtripbscFv(CEA6) without DMSI, H6FXtripbscFv(CEA6) with 0.5 mg/ml DMSI (lane 2), H6FXtripbscFv(CEA6) with 1.0 mg/ml DMSI (lane 3), H6FXtripbscFv(CEA6) with 1.5 mg/ml DMSI (lane 4) and H6FXtripbscFv(CEA6) with 2.0 mg/ml DMSI (lane 5). Protein marker of 94, 68, 43, 30, 20, and 14.4 kDa, top to bottom (lane M). Lane 6: TN123 without DMSI, TN123 with 0.5 mg/ml DMSI (lane 7), TN123 with 1.0 mg/ml DMSI (lane 8) TN123 with 1.5 mg/ml DMSI (lane 9) and TN123 with 2.0 mg/ml DMSI (lane 10).

DETAILED DISCLOSURE OF THE INVENTION

The term "trimerising structural element" (TTSE) used in the present description and claims is intended to refer to the portion of a polypeptide molecule of the tetranectin family which is responsible for trimerisation between monomers of the tetranectin polypeptide. The term is also intended to embrace variants of a TTSE of a naturally occurring tetranectin family member, variants which have been modified in the amino acid sequence without adversely affecting, to any substantial degree, the trimerisation properties relative to those of the native tetranectin family member molecule. Specific examples of such variants will be described in detail herein, but it is generally preferred that the TTSE is derived from human tetranectin, murine tetranectin, C-type lectin of bovine cartilage, or C-type lectin of shark cartilage. Especially preferred is monomer polypeptide constructs including at least one TTSE derived from human tetranectin.

The 49 residue polypeptide sequence encoded by exons 1 and 2 of tetranectin (FIG. 1) appears to be unique to the tetranectin group of proteins (FIG. 2) as no significant sequence homology to other known polypeptide sequences has been established. In preparation for experimental investigations of the architecture of tetranectin a collection of recombinant proteins was produced, the collection including complete tetranectin, the CRD domain (approximately corresponding to the polypeptide encoded by exon 3), a product corresponding to the polypeptide encoded by exons 2+3, a product corresponding to exons 1+2 (Holtet et al., 1996; Example 2). As detailed in Example 2 we now know differently: tetranectin is indeed a trimer, but the exon 2 encoded polypeptide is in fact capable of effecting trimerisation by itself as evidenced by the observation that the recombinant protein corresponding to exons 2+3 is in fact trimeric in solution.

3D-structure analysis of crystals of full-length recombinant tetranectin (Nielsen et al., 1996; Nielsen, 1996; Larsen et al., 1996; Kastrup, 1996) has shown that the polypeptide encoded in exon 2 plus three residues encoded in exon 3 form a triple alpha helical coiled coil structure.

From the combination of sequence and structure data it becomes clear that trimerisation in tetranectin is in fact generated by a structural element (FIG. 2), comprising the amino acid residues encoded by exon two and the first three residues of exon 3 by an unusual heptad repeat sequence, that apparently is unique to tetranectin and other members of its group: This amino acid sequence (FIG. 2) is characterised by two copies of heptad repeats (abcdefg) with hydrophobic residues at a and d positions as are other alpha helical coiled coils. These two heptad repeats are in sequence followed by an unusual third copy of the heptad repeat, where glutamine 44 and glutamine 47 not only substitute the hydrophobic residues at both the a and d position, but are directly involved in the formation of the triple alpha helical coiled coil structure. These heptad repeats are additionally flanked by two half-repeats with hydrophobic residues at the d and a position, respectively.

The presence of beta-branched hydrophobic residues at a or d positions in alpha helical coiled coil are known to influence the state of oligomerisation. In the tetranectin structural element only one conserved valine (number 37) is present. At sequence position 29 in tetranectin no particular aliphatic residue appears to be preferred.

In summary, it is apparent that the triple stranded coiled coil structure in tetranectin to a large extent is governed by interactions that are unexpected in relation to those characteristic among the group of known coiled coil proteins.

The TTSEs form surprisingly stable trimeric molecules. (Examples 2, 3 and 4). The experimental observations, that (1) a substantial part of the recombinant proteins exists in the oligomeric state of—and can be cross-linked as—trimeric molecules even at 70° C. and (2) that exchange of monomers between different trimers can only be detected after exposure to elevated temperature are evidence of a extremely high stability of the tetranectin trimerising structural element. This feature must be reflected in the amino acid sequence of the structural element. In particular, the presence and position of the glutamine containing repeat in the sequential array of heptad repeats is, together with the presence and relative position of the other conserved residues in the consensus sequence (FIG. 2), considered important for the formation of these stable trimeric molecules. For most practical uses the cysteine residue 50 should be mutagenized to serine, threonine, methionine or to any other amino acid residue in order to avoid formation of an unwanted inter-chain disulphide bridge, which eventually would lead to uncontrolled multimerisation, aggregation and precipitation of a polypeptide product harbouring this sequence.

In particular in conjunction with the trimer-stabilising exon 1 encoded polypeptide (tetranectin residues 1 to 16, see Example 2), the tetranectin trimerising structural element is a truly autonomous polypeptide module retaining its structural integrity and propensity to generate a highly stable homotrimeric complex whether it is attached or not by a peptide bond at either or at both termini to other proteins. This unique property is demonstrated in the accompanying examples, which provide experimental proof, that polypeptide sequences derived from heterologous proteins may readily be trimerised when joined as fusion proteins to the tetranectin trimerising structural element. This remains valid irrespective of whether the heterologous polypeptide sequences are placed amino-terminally or carboxy-terminally to the trimerising element allowing for the formation of one molecular assembly containing up to six copies of one particular polypeptide sequence or functional entities, or the formation of one molecular assembly containing up to six different polypeptide sequences, each contributing their individual functional property.

Since three TTSEs of naturally occurring human tetranectin forms up a triple alpha helical coiled coil, it is preferred that the stable complex formed by the TTSEs of the invention also forms a triple alpha helical coiled coil.

The "tetranectin family" are polypeptides which share the consensus sequence shown in FIG. 2 or a sequence which are homologous at sequence level with this consensus sequence. Hence, monomer polypeptide constructs of the invention are preferred which comprise a polypeptide sequence which has at least 68% sequence identity with the consensus sequence shown in FIG. 2, but higher sequence identities are preferred, such as at least 75%, at least 81%, at least 87%, and at least 92%.

By the term "heterologous moiety" is herein meant any chemical entity which can be linked covalently to a TTSE and to which the TTSE is not natively covalently bound. Hence, the heterologous moiety can be any covalent partner moiety known in the art for providing desired binding, detection, or effector properties. The heterologous moiety can be a ligand binding structure such as a receptor molecule or the ligand binding part of a receptor molecule, an antibody, an antigen binding antibody fragment, or a molecule having antibody characteristics such as e.g. the "diabodies" described in EP-A-0 672 142, or other ligand binding molecules such as avidin or streptavidin, or a lectin; a toxin such as ricin; a detectable label such as a fluorescence labelled molecule, a radioactively labelled molecule, an enzymatically labelled molecule; an in situ activatable substance, such as a molecule which can be induced by a magnetic field or by radiation to be radioactively or chemically active; an enzyme such as a peroxidase; a radioactive moiety such as a γ-, α-, β⁻-, or β⁺-emitting molecule, e.g. a molecule comprising one or more radioactive isotopes selected from $^{14}C$, $^{3}H$, $^{32}P$, $^{33}P$, 25S, 38S, $^{36}Cl$, $^{22}Na$, $^{24}Na$, $^{40}K$, $^{42}K$, $^{43}K$, and any isotopes conventionally utilized for the purposes of facilitating detection of probes or the purposes of providing localized radiation so as to effect cell death; a cytokine such as an interferon or a leukotriene; PNA; a non-proteinaceous polymer such as a polymeric alkaloid, 11.a polyalcohol, a polysaccharide, a lipid and a polyamine; a photo cross-linking moiety, i.e. a chemical entity which effects cross-linking upon photo-activation; and a group facilitating conjugation of the monomer polypeptide construct to a target.

The heterologous moiety is preferably covalently linked to the TTSE by via a peptide bond to the N- or C-terminus of the TTSE peptide chain, via a peptide bond to a side chain in the TTSE or via a bond to a cysteine residue, but any way of coupling covalently heterologous material to a polypeptide chain will be useful. The skilled person will know of such possibilities, e.g. by consulting the teachings of WO 95/31540 in this regard which are hereby incorporated by reference.

However, one interesting aspect of the invention relates to a monomer polypeptide construct of the invention comprising two heterologous moieties which are linked via peptide bonds to the N- and C-terminus, respectively. This approach introduces a number of possibilities in terms of e.g. linking larger entities with oligomers of the invention by having specific activities coupled to each end of the monomers (as explained in detail below, the oligomers of the invention may also utilise a version of this principle, where e.g. one N-terminus and one C-terminus of an oligomer are linked via peptide bonds to independent heterologous moieties).

In general, a complex between two or three monomers are described in the following way: three monomers having one TTSE each forms a trimer designated (1+1+1), whereas a dimer formed between a monomer with two TTSEs and a monomer with one TTSE is designated (1+2). Other (undesired) trimers can of course be formed, e.g. (2+2+1), where two TTSEs are not "in use", but it is preferred that the oligomers of the invention use all of their available TTSEs during complex formation. It should also be noted that the term "monomer polypeptide construct" is meant to designate a single polypeptide chain which may or may not have nonpeptide groups coupled covalently to the polypeptide chain, whereas "dimeric polypeptide" or "dimer", "trimeric polypeptide" or "trimer" and "oligomer" (i.e. a dimer or trimer) in the present context are meant to designate noncovalent complexes of monomer polypeptide constructs. I.e., the traditional definitions of monomers and multimers do not apply in the present specification and claims.

The TTSE as exemplified by exon 2 or exons 1 and 2 of human tetranectin, preferably so modified to allow only hetero-trimerisation between dissimilar (1+1+1) or (1+2) (cf. the below discussion) subunits may be deployed as a general affinity mediator, which can be coupled chemically to each member of a selection of target molecules. After such conjugation with TTSE the target molecules may be homo- or heterotrimerised as desired for any application. Similar deployment of dimerisation, using as one partner a polypeptide harbouring two TTSE sequences in-line, separated by a linker sequence of suitable length and character, may bet yet more advantageous, as in such case absolute control of stoichiometry in complex formation would be possible. Thus, an important embodiment of the invention is a monomer polypeptide construct of the invention comprising 2 TTSEs which are covalently linked by a spacer moiety which allows both of the 2 TTSEs to take part in complex formation with a third TTSE not being part of the monomer polypeptide construct, but equally important is the embodiment of the invention where the monomer polypeptide construct comprises one single TTSE, so as to allow trimerisation between three monomers and hence providing the optimum degree of versatility with respect to the number of functional units which can be easily incorporated into one single complex.

In the embodiments where two TTSEs are present in the same monomer it is preferred that the spacer moiety has a length and a conformation which favours complex formation involving both of the two TTSEs which are covalently linked by the spacer moiety. In this way, problems arising from undesired formation of trimers of the formats (2+1+1), (2+2+2), and (2+2+1) (wherein only one TTSE of each monomer participates in complex formation) can be diminished. Design and preparation of suitable spacer moieties are known in the art and are conveniently effected by preparing fusion polypeptides having the format $TTSE^1$-Spacer-$TTSE^2$, where the spacer moiety is a polypeptide fragment (often a relatively inert one), so as to avoid undesired reactions between the spacer and the surroundings or the TTSEs.

One typical scenario, where such modification may be advantageous is the case of immunological detection where a chemical conjugate of an antibody with enzymes such as peroxidase is used for in situ staining purposes in tissue or on western blots.

A similar, but yet different, application example would be the deployment of TTSE to mediate conjugation of e.g. alkaline phosphatase and an oligonucleotide which would allow in situ identification of a given mRNA in a tissue sample concurrently with identification of any other mRNA molecule e.g. by interconnection of a second appropriate oligonucleotide and a signalling/visualisation molecule using e.g. the biotin—avidin/streptavidin affinity pair for conjugation. The point of having two or more selective affinity systems available for conjugating oligonucleotide probes and detector molecules is that as many different sequences may be detected simultaneously as there are affinity sets available.

In terms of chemistry required to exploit TTSE as a conjugating affinity-contributing agent, the peptide corresponding to exon 2 will have a sufficient affinity for most purposes, but incorporation of all, or some segment of the exon 1 polypeptide will serve to increase affinity and stability. The properties of tetranectin mutants in which many of hydrophilic (e.g. lys and glu) residues that are largely exterior in the coiled coil structure have been replaced with alanine appear similar to the native protein, suggesting that is indeed possible without interfering very much with stability of the trimeric structure to replace all glu, asp and lys residues by a combination of gln, asn, arg or ala, and thereby generate a sequence that, as an N-terminally blocked synthetic peptide, would be very easy to convert into a chemically stable active-ester component, e.g. an N-hydroxy succinimide ester of an acetylated peptide, that could react with (and thereby couple to) any exposed lysine side chain in a target molecule of interest. Such peptide synthesis, activation and coupling chemistry will be readily designed and applied by a person skilled in the art of peptide chemistry, as will indeed any other conjugation chemistry, like the attachment and use of photo-activatable moieties like e.g. phenyl azides.

In conclusion, it seems that the most important structure in native TTSE is the consensus sequence shown in FIG. 2, and that large variations in the polypeptide chain may be allowed. Hence, one advantageous embodiment of the monomer polypeptide construct of the invention is one where at least one amino acid residue selected from the group consisting of amino acid residue nos. 6, 21, 22, 24, 25, 27, 28, 31, 32, 35, 39, 41, 42, is/are substituted by any non-helix breaking amino acid residue, the amino acid residue numbering referring to amino acid residues in SEQ ID NO: 7. All these residues have been shown not to be directly involved in the intermolecular interactions which stabilises the trimeric complex between three TTSEs of native tetranectin monomers and it is therefore expected that these amino acids may be safely substituted with any amino acid which will not have an adverse effect on helix formation (notably proline, which introduces a rigid bend in a polypeptide chain).

Another advantageous embodiment of the monomer polypeptide construct of the invention is one which is free from any free amino and/or carboxy groups. This would favour synthesis of a TTSE by means of solid or liquid phase peptide synthesis, since there would be no need of introducing any protective groups during peptide synthesis.

Since the consensus sequence of FIG. 2 is believed important and since this consensus sequence embraces the above-discussed heptad repeat, it is according to the invention preferred that the TTSE comprises a repeated heptad having the formula a-b-c-d-e-f-g (N to C), wherein residues a and d generally are hydrophobic amino acids. However, since “a” and “d” in the third of the complete heptads of all known members of the tetranectin family are constituted of glutamine, it is most preferred that the TTSE comprises the heptad repeated 3 times and that the last occurrence of the heptad has a glutamine residue corresponding to residues a and d.

Since exon 2 of native members of the tetranectin family seems to contain the necessary elements to effect stable trimerisation, it is preferred that the monomer polypeptide construct is free of substantial parts of tetranectin which is encoded by exon 3 and/or lacks substantial parts of tetranectin which is encoded by exon 1. However, since exon 1 encoded material seems to stabilise the trimeric native tetranectin, it is especially preferred that all or part of exon 1 is part of the monomer polypeptide construct, and it also seems to be rational to include the first three amino acids encoded by exon 3, since these are known to take part of the formation of the native triple alpha helical coiled coil in human tetranectin.

One particularly interesting embodiment of the invention is the possibility of designing oriented molecular assemblies, where one or more functional entities are located N-terminally to the trimerising element and one or more functional entities are located C-terminally to the element. Such types of design may be particularly advantageous where a certain relative ratio is desired among the different functional entities included in a specific molecular unit. Such type of design may in addition be used if one or more functional entities for either structural or functional reasons appear incompatible within the same construct. Such may be the case if one or more of the functional entities are expressed by large or bulky protein domains which for steric reasons might prevent formation of the trimeric molecular unit due to sterical constraints.

The possibility of constructing bi-polar three-way fusion proteins in which one functionality is placed N-terminally to the coiled coil structure and a different functionality is placed C-terminally is additionally advantageous in applications where large spatial separation between the two functionalities are desirable for optimal function. Examples of such application are e.g. the deployment of binding domains (e.g. antibody-derived binding modules) for recognition and binding to binding sites located at or close to large structures like cell membranes in cases where it is advantageous to allow for binding of the other end of the trimerised molecule to a different, but also bulky target.

Hence, as discussed above, the oligomers of the invention may be used to join e.g. bulky surfaces by the oligomer according to the invention comprising at least one heterologous moiety which is positioned N-terminally to a TTSE and at least one heterologous moiety which is positioned C-terminally to a TTSE. The two heterologous moieties can be either part of the same monomer polypeptide construct or parts of two separate monomer polypeptide constructs.

The extraordinarily high stability of any trimer containing the tetranectin trimerisation module under physiological buffer and temperature condition (i.e. absence of denaturant, temperature not exceeding 40° C.) in combination with the ease by which exchange of monomer subunits between trimers can be effected by incubation at moderately elevated temperature or in the presence of denaturants provide for a unique opportunity to deploy the trimerisation module as a vehicle to allow the construction of "pick-and-mix" conjugates prepared from previously fabricated collections of homotrimeric molecules. To illustrate the versatility of this design opportunity by way of theoretical example, let us assume that (1) a collection of twenty different antibody constructs (e.g. in the format of single-chain Fv) each of its own characteristic binding specificity, has been selected and then turned into homo-trimeric molecules by fusion to a tetranectin trimerisation module, and let us also assume that a set of twenty different effector molecules (e.g. toxin domains) have similarly been prepared and also conjugated to the tetranectin trimerisation module. A user provided with prefabricated collections of twenty different antibody constructs and twenty different toxin constructs—40 different reagents in all—has the opportunity then to prepare 400 different toxin-antibody conjugates, simply by mixing a first preferred component from one reagent collection with a second preferred reagent from the other collection and then subject this binary mixture to conditions, i.e. gentle heating or incubation with a suitable level of denaturant, to accomplish subunit exchange among all trimeric molecular species in the mixture. After the subunit exchange step the desired hetero-bifunctional reagent will be present in the mixture as a major component of the mixture and may then be deployed as such to accomplish a given purpose or, alternatively apply a simple purification step to isolate his favoured hetero-functional binary reagent from any remaining mono-functional trimer species by a simple standard protein purification step, easily designed using standard techniques known in the field of protein purification.

A further enhancement of the versatility of the "pick-and-mix" technology may be achieved by including a specific affinity purification tag on each array of trimerisation module—probe/effector/indicator conjugate, fused directly in-line or, alternatively, fused via a cleavable linker (a polypeptide segment containing e.g. a factor $X_a$ or an enterokinase recognition/cleavage site) to the affinity tag. More specifically, if each of three libraries were tagged with affinity handles a, b and c, respectively, that were recognised by binding substances A, B and C, respectively, pure heterotrimers, composed of one member of each library, could be obtained in a three-step affinity purification procedure designed to allow selective recovery of only such trimers that exhibit affinity for substances A and B and C. If, for any reason, subsequent removal of the affinity tags were desirable, and the constructs had been prepared to include cleavable linkers, isolation of the pure heterotrimer, liberated from all affinity tags, could be accomplished by three further affinity purification steps, arranged to isolate only material that would bind to neither substance A nor substance B nor substance C.

Obviously, the scope of "pick-and-mix" design of user-preparable heterofunctional complexes apply not only to the formation of binary hetero-functionality, but would apply by logic extension to the formation of ternary hetero-functionality: To envisage the wealth of possibilities that are inherent to the concept of ternary hetero-functionality in a further theoretical example along the lines given above, three sets of reagent collections, each comprising 20 different functional characteristics, i.e. a collection of in toto 60 different homotrimers would allow "pick-and-mix" preparation of 8,000 different tri-functional molecules.

The basic tetranectin trimerisation module will, essentially indiscriminately, form homo- and hetero-trimers with any molecule that also contains a trimerisation module. For some applications it may be advantageous to have available specially engineered derivatives of the tetranectin trimerisation module, which have been reengineered to disallow homotrimer formation and hence only allow hetero-trimerisation. Thus, an important embodiment of the monomer polypeptide construct of the invention is constructed/reengineered so as to disfavour formation of complexes between identical TTSEs; this also has the implication that oligomers of the invention can advantageously be comprised of monomer polypeptide constructs which are designed so as to disfavour formation of trimers including two monomer polypeptide constructs having identical TTSEs. One way of disfavouring the formation of homotremerisation would be by "knobs into holes" mutagenisis.

The design/reengineering may be accomplished by introduction of amino acid substitution at sites in the polypeptide intimately involved in the formation and stability of the trimer and, simultaneously, in a different construct introduce a compensatory amino acid substitution, all in all removing symmetry between individual monomer components of the triple helical structure so that the structural complementarity profile only allows the formation of hetero-trimers, but is incompatible with some or each of the homotrimer species.

A yet different way to deploy the tetranectin trimerisation module as a vehicle to accomplish rational formation of bifunctionalisation would require the interconnection of the C-terminus of one monomer to the N-terminus of a second monomer in the triple-helical structure. The basic requirement for such an intervening polypeptide is, that allowed spatial distances between its N- and C-termini must be compatible with the spacing inherent to the structural requirements given by the architecture of the tetranectin trimerisation module. The construction of an intervening connecting polypeptide allowed according to such criteria would be readily accomplished by an average person skilled in the art of protein engineering, as an ample collection of examples of the deployment of, usually flexible, spacer sequences are known both in nature and in designed proteins. Due to the expected entropic contribution to interaction energy in a molecule in which two of the three tetranectin trimerisation module components are covalently tied together, such a molecule would show great preference for selecting any molecule containing only a single copy of the tetranectin trimerisation module component, as this selection would be energetically favoured. Hence, conjugation of one functional protein component to a suitably selected covalently dimerised tetranectin trimerisation module component and conjugation of a different functional protein component to a single-copy element of the trimerisation sequence would provide for the preferential formation of a 1:1 bifunctional complex and suppression of formation of any other complex.

The monomers of the invention may be prepared by methods generally known in the art, using exclusively or in combination the techniques of recombinant protein production, peptide synthesis (liquid phase or solid phase), and traditional chemical coupling of heterologous moieties to a peptide chain or to specific residues therein. Hence the invention also relates to a method of preparing the monomer polypeptide construct of the invention, the method comprising isolating the monomer polypeptide construct from a culture comprising a host cell which carries and expresses a nucleic acid fragment which encodes the monomer polypeptide construct, synthesizing, by means of chemical peptide synthesis, the monomer polypeptide construct and subsequently isolating the monomer polypeptide construct from the reaction mixture, preparing a TTSE in a culture comprising a host cell which carries and expresses a nucleic acid fragment which encodes the TTSE, subsequently linking covalently at least one heterologous moiety to the TTSE, and thereafter isolating the resulting monomer polypeptide construct, or synthesizing, by means of chemical peptide synthesis, a TTSE, subsequently linking covalently at least one heterologous moiety to the TTSE, and thereafter the isolating the resulting monomer polypeptide construct from the reaction mixture, and optionally subjecting the monomer polypeptide construct to further processing.

The nucleic acid fragment which is mentioned above is also a part of the invention and is defined as a nucleic acid fragment in isolated form which encodes a TTSE as defined herein or which encodes the polypeptide part of a monomer polypeptide construct according to the invention, with the proviso that the nucleic acid fragment is different from one that encodes native members of the tetranectin family, and that the nucleic acid fragment is different from one that encodes any of the fusion proteins CIIH6FXTN123, H6FXTN123, H6FXTN12, H6FXTN23, the sequences of which are shown in SEQ ID NOs: 24-27.

The above mentioned host cell (which is also a part of the invention) can be prepared by traditional genetic engineering techniques which comprises inserting a nucleic acid fragment (normally a DNA fragment) encoding the polypeptide part of a monomer polypeptide construct of the invention into a suitable expression vector, transforming a suitable host cell with the vector, and culturing the host cell under conditions allowing expression of the polypeptide part of the monomer polypeptide construct. The nucleic acid fragment encoding the polypeptide may be placed under the control of a suitable promoter which may be inducible or a constitutive promoter. Depending on the expression system, the polypeptide may be recovered from the extracellular phase, the periplasm or from the cytoplasm of the host cell.

Suitable vector systems and host cells are well-known in the art as evidenced by the vast amount of literature and materials available to the skilled person. Since the present invention also relates to the use of the nucleic acid fragments of the invention in the construction of vectors and in host cells, the following provides a general discussion relating to such use and the particular considerations in practising this aspect of the invention.

In general, of course, prokaryotes are preferred for the initial cloning of nucleic sequences of the invention and constructing the vectors useful in the invention. For example, in addition to the particular strains mentioned in the more specific disclosure below, one may mention by way of example, strains such as *E. coli* K12 strain 294 (ATCC No. 31446), *E. coli* B, and *E. coli* X 1776 (ATCC No. 31537). These examples are, of course, intended to be illustrative rather than limiting.

Prokaryotes are also preferred for expression, since efficient purification and protein refolding strategies are available. The aforementioned strains, as well as *E. coli* W3110 (F-, lambda-, prototrophic, ATCC No. 273325), bacilli such as *Bacillus subtilis*, or other enterobacteriaceae such as *Salmonella typhimurium* or *Serratia marcesans*, and various *Pseudomonas* species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used. *Saccharomyces cerevisiase*, or common baker's yeast is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3- phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

Upon production of the polypeptide monomer constructs it may be necessary to process the polypeptides further, e.g. by introducing non-proteinaceous functions in the polypeptide, by subjecting the material to suitable refolding conditions (e.g. by using the generally applicable strategies suggested in WO 94/18227), or by cleaving off undesired peptide moieties of the monomer (e.g. expression enhancing peptide fragments which are undesired in the end product).

In the light of the above discussion, the methods for recombinantly producing the monomer polypeptide construct of the invention are also a part of the invention, as are the vectors carrying and/or being capable of replicating the nucleic acids according to the invention in a host cell or a cell-line. According to the invention the expression vector can be e.g. a plasmid, a cosmid, a minichromosome, or a phage. Especially interesting are vectors which are integrated in the host cell/cell line genome after introduction in the host.

Another part of the invention are transformed cells (useful in the above-described methods) carrying and capable of replicating the nucleic acid fragments of the invention; the host cell can be a microorganism such as a bacterium, a yeast, or a protozoan, or a cell derived from a multicellular organism such as a fungus, an insect cell, a plant cell, or a mammalian cell. Especially interesting are cells from the bacterial species *Escherichia*, *Bacillus* and *Salmonella*, and a preferred bacterium is *E. coli*.

Yet another part of the invention relates to a stable cell line producing the polypeptide part of a monomer polypeptide construct according to the invention, and preferably the cell line carries and expresses a nucleic acid of the invention.

On the basis of the above discussions it will be clear to the skilled person that also the oligomers resulting from the complex formation between the monomer constructs of the invention are important parts of the invention. Hence the invention also pertains to an oligomer which is comprised of two monomer polypeptide constructs according to the invention which comprises at least three TTSEs, or which is comprised of three monomer polypeptide constructs according to the invention which each only contain one single TTSE.

As is explained herein and shown in the examples, the oligomers of the invention are stable at temperatures up to 70° C. and it is therefore especially preferred that the oligomers of the invention are stable at temperatures above physiological ones, e.g. that the oligomers are stable in the temperature range 50-70° C.

Also a part of the invention is a method for preparing a dimeric oligomer of the invention which comprises
- admixing a monomer polypeptide construct which includes two TTSEs (construct 1) with a monomer polypeptide construct which includes only one TTSE (construct 2),
- effecting the two TTSE's of construct 1 to complex with the TTSE of construct 2 (this can be done by thermal treatment, i.e. heating to a temperature which ensures denaturation followed by subsequent cooling allowing renaturation, or this can be done by denaturing/renaturing effected by changes in the chemical environment), and
- isolating the resulting dimer and optionally subjecting the dimer to further processing (cf. the above discussion of further processing, but it should also be mentioned that the further processing could include non-covalent coupling of interesting and relevant moieties to the dimeric oligomer).

Consequently, the method for producing a trimeric oligomer is also a part of the invention and comprises the steps of
- admixing three monomer polypeptide constructs of the invention with each other,
- effecting complex formation between one TTSE of each monomer polypeptide construct, and
- isolating the resulting trimer and optionally subjecting the trimeric oligomer to further processing.

The considerations applying to complex formation and further processing mentioned above apply to this method also.

In view of the detailed discussion above of the "pick-and-mix" aspect of the invention, the invention also pertains to a kit comprising
- a first package comprising at least one container means, each at least one container means containing a monomer polypeptide construct of the invention,
- a second package comprising at least one container means, each at least one container means in the second package containing a monomer polypeptide construct of the invention, the second package being different from the first package with respect to choice and/or number of monomer polypeptide constructs included therein, and optionally
- a third package comprising at least one container means, each at least one container means in the third package containing a monomer polypeptide construct of the invention, the second package being different from the first and second packages with respect to choice and/or number of monomer polypeptide constructs included therein.

It is preferred that the at least one container means in each package contains mutually distinct monomer polypeptide constructs, and it is especially preferred that all container means comprised in the kit comprises mutually distinct polypeptide constructs.

A very important aspect of the invention is the possibility of generating a system designed especially for the individual circumstances. The basic idea is that the artificial selection of heterologous moieties and optionally active components, and functional entities result in a unique system as will be further disclosed in the following.

Using the TTSE as a vehicle for assembling monovalent scFv or Fab antibody fragments into oligomeric and multivalent entities offer design advantages also in terms of generating chimaeric artificial antibodies having desirable pharmacokinetic and pharmacodynamic properties. Small derivatives like monomeric scFv fragments or bivalent "minibodies" are rapidly cleared from the circulatory system, whereas complete Igs stay for very much longer. Conversely, small derivatives like scFv and minbodies exhibit better extravasation properties. It is therefore expected that antibodies of a desired specificity may be optimized for particular diagnostic or therapeutic needs by engineering the pharmacological properties, using the TTSE as a vehicle for controlled oligomerization of e.g. scFv fragments.

One example of such engineering would be the requirements for delivering a high dose of an imaging or toxin-conjugated antibody to a tumour, while ensuring as low a systemic exposure or imaging background as possible. In such case a TTSE conjugated scFv fragment could be designed to exhibit strong multivalent binding to the tumour and rapid clearance of excess conjugate from circulation.

Accordingly, in af further aspect the present invention also relates to the use of a monomer polypeptide construct or to a an oligomer according to the present invention as a vehicle for assembling antibody fragments into oligomeric or multivalent entities for generating chimeric artificial antibodies having preselected pharmacokinetic and/or pharmadynamic properties.

The use of specific delivery systems also play an important role in connection with the present invention in that such systems may by utilized with respect to different use of the present invention both with respect to the a more general therapeutic application and with respect to gene therapy. Examples of suitable drug delivery and targeting systems are disclosed in Nature 392 supp. (30 Apr. 1998).

Accordingly, efficiency of deliverance may be further increased if the delivery system e.g a liposome is supplied with a molecular unit, an "infector or transfector" ligand, recognized by a internalizing receptor unit specific for the target cells. For example, cells displaying endocytotic receptors like members of the LDL family of receptors may be even more efficiently infected or transfected either by including a TTSE unit in the antibody containing heterorimer or in an independent TTSE unit conjugated to one or more of the domains of the Receptor Associated Protein, RAP, (Ellgaard, L., Holtet, T. L., Nielsen, P. R., Etzerodt, M., Gliemann, J. & Thøgersen, H. C. Eur J Biochem. 1997, vol 244, 544-551) which is recognized as a ligand to all receptors in this abundant family of endocytosis-mediating receptors.

Accordingly, in a further aspect, the invention is directed to the use of a monomer polypeptide construct or to an oligomer according to the invention for targeted gene therapy involving selective delivery of the material for transfection or infection of the specific population of cells.

The ultimate perspective of such TTSE-mediated gene therapy would be the deployment of a viral vector that would find no other targets in the patient but the cells displaying the artificial receptor complex.

In a still further aspect, the invention is directed to the use of a monomer polypeptide construct or to a an oligomer construct according to the invention wherein the at least one heterologous moiety comprises a moiety selected from a ligand binding structure such as a receptor molecule or the ligand binding part of a receptor molecule, and wherein the gene therapy involves the delivery of nucleic acids to the desired population of cells by use of a viral vector directed to cells displaying the artificial receptor complex corresponding to the heterologous moiety.

In another aspect, the invention is directed to the use of a monomer polypeptide construct or to a an oligomer construct according to the invention wherein at least one TTSE is modified with a membrane integrating or associating entity having affinity to the specific population of cells in the body relevant for the gene therapy.

Furthermore, a recent review of the imaging an therapeutic potential of a range of known antibody derivatives has been published by Paul Carter and Margaret Merchant of Genentech Inc. (Current Opinion in Biotechnology, 1997, vol 8, 449-454). In direct continuation of their conclusions it will be apparent that oligomersation of antibody derivatives like scFv derivatives may extend current technology in the designer-antibody field in many important aspects, some of which will be elaborated below (with reference to the Carter & Merchant review).

One of the well-known problems inherent to mouse monoclonal antibodies that have been 'humanized' by grafting of the murine antigen combining site onto a human Ig framework is that antigenicity of the chimaeric product in human patients is often difficult to suppress entirely, resulting in—sometimes life-threatening—immune reactions to the diagnostic or therapeutic humanized antibody product. The risk of such side-effects are expected to be much reduced if the designer antibody is assembled from purely human proteins or protein fragments. Since the TTSE trimerising unit described here is identical to a portion of human tetranectin that is already present in human plasma and tissue, there is good reason to expect that the TTSE will not elicit an antigenic response in a human subject if it is introduced as a component of a chimaeric product that is not otherwise antigenic in humans.

Accordingly, in one aspect, the present invention relates to the use of a monomer polypeptide construct or to a an oligomer according to the present invention as a component of a chimaeric product having low antigenicity in humans relative to formulations comprising on or more components of non-human origin.

Carter & Merchant further review present technology for radiolabelling of antibody derivatives. Again, oligomerisation using TTSEs offer more elegant solutions to problems associated with labelling, as the TTSE offers the possibility to construct one or two of the TTSE monomer units in a heterotrimeric complex to harbour the site carrying the label. Thus, in this format labelling may also be confined to the non-antibody part of the complex, leaving the antigen-binding module entirely unmodified, and the complex may furthermore be formulated "in the field" as and when needed.

In many receptor-mediated signal transduction pathways signals are triggered by the clustering of receptor molecules on the cell membrane. The TTSEs therefore have important applications in the study and exploitation of receptor signalling, as ligands may be presented as oligomers by conjugation to a TTSE unit.

This also has important application in phage display technologies for discovering new ligands and new receptors as the engineering of a TTSE unit fused inline to a candidate ligand molecule will allow the display of a hetero-trimeric phage coat protein, in which only one of the monomer units is conjugated to the phage coat protein. This may be accomplished by appropriate insertion of amber codons at the site of fusion of phage coat protein to the TTSE-ligand segment of the three-way fusion protein encoded by the recombinant phage. In appropriate *E. coli* cells the presence of this amber codon will result in translation termination in the majority of read-throughs, and hence most of the fusion protein product secreted to the periplasmic compartment in the phage-infected bacterium will be soluble TTSE-ligand fusion protein, whereas a minority of the fusion protein will also contain a phage protein module. The majority of trimers that will be generated will therefore contain, at most, one monomeric unit that will ensure integration (display) in the mature recombinant phage particle.

A further advantage of the display technology described above relates to the fact that it is specially useful for selection on the basis of a relatively low affinity because of the entropic benefit contribution obtained by the proximity of the tree binding moieties in confined spatial arrangement.

Accordingly, the present invention in an important aspect, also relates to protein library technology wherein the TTSE's described above are utilized.

The trimerisation of candidated recombinant ligands is especially important as, for many receptors, the intracellular signal is induced by receptor clustering, which is only brought about if the external ligand exhibits multivalent binding to the receptor, so as to bridge two or more receptor molecules.

In one preferred embodiment the monomer polypeptide construct or the oligomer construct according to the invention is for targeted gene therapy involving selective delivery of the material for transfection or infection of the specific population of cells. The at least one heterologous moiety may comprise a moiety selected from a ligand binding structure such as a receptor molecule or the ligand binding part of a receptor molecule, and wherein the gene therapy involves the delivery of nucleic acids to the desired population of cells by use of a viral vector directed to cells displaying the artificial receptor complex corresponding to the heterologous moiety.

As mentioned above, it is an important aspect of the invention that the monomer polypeptide construct and/or the oligomer may be used as a component of a chimaeric product having low antigenicity in humans. As the construct is of human origin it is believed that the antigenicity in humans is low relative to formulations comprising on or more components of non-human origin.

One primary use of a monomer polypeptide construct or a an oligomer according to the invention is for delivering an imaging or toxin-conjugated antibody to a target such as a tumor, or use as a vehicle delivering an substance to a target cell or tissue, as a vehicle for assembling antibody fragments into oligomeric or multivalent entities for generating chimeric artificial antibodies having preselected pharmacokinetic and/or pharmadynamic properties.

The substance in question being one or more selected from the group of heterologous moieties as well a pharmaceutical. Also a labelled construct wherein the label is coupled to one or to of the TTSE monomer units is within the scope of the invention.

As explained in detail previously, an important and surprising use of the monomer polypeptide construct or the oligomer according to the present invention is for protein library technology, such as phage display technology. The present invention also relates to any polynucleotide molecule such as a RNA, DNA or PNA as well as any vector encoding one or more TTSE.

A further use according to invention includes preparation and use of a pharmaceutical composition comprising the TTSE construct and optionally a pharmaceutically acceptable excipient. The composition may be administered by a route selected from the group consisting of the intraveneous route, the intraarterial route, the transmembranes route of the buccal, anal, vaginal or conjunctival tissue, the intranasal route, the pulmonary route, the transdermal route, the intramuscular routed, subcutaneous route, intratechal route, inoculation into tissue such as a tumour, or by an implant.

The monomer polypeptide construct or the oligomer is in a preferred embodiment comprised in a liposome.

It is obvious from the disclosure of the present invention that the treating or preventing of a disease may by a further aspect comprising administering to the subject in need thereof an effective amount of a pharmaceutical composition referred to above.

In one aspect of the various possibilities according to the present invention concerning how the human gene therapy is targeted, includes the case wherein at least one TTSE is modified with a membrane integrating or associating entity having affinity to the specific population of cells in the body relevant for the gene therapy.

As used in the conventional pharmaceutic field the present invention includes a method wherein the monomer polypeptide construct or the oligomer is administered by a route selected from the group consisting of the intraveneous route, the intraarterial route, the transmembranes route of the buccal, analog vaginal tissue, intranasal route, the pulmonary route, the transdermal route, intramuscular, subcutaneous, intratechal, the buccal, inoculation into tissue such as a tumour, or by an implant.

Finally, the present invention is also relating to the field of diagnosing as the skilled person would easily recognize, that the TTSE disclosed in the present invention may also refer to a method for diagnosis comprising a construct comprising the monomer polypeptide construct or the oligomer, together with a diagnosing component coupled thereon.

Example 1

Design and Construction of the pTH6trip *E. coli* Expression Vectors for the Production of Trimerised Chimeric Fusion Proteins The plasmid clone pT7H6FXTN123 (Example 2) was used as template for amplification in two Polymerase Chain Reactions (PCR) (Saiki et al., 1988) with the primer pairs trip-N (SEQ ID NO: 1) and trip-Ca (SEQ ID NO: 2) and trip-N (SEQ ID NO: 1) and trip-Cb (SEQ ID NO: 3), respectively. The amplified DNA fragments, tripa, comprising nucleotide sequences encoding an IQGR cleavage site for the restriction protease $FX_a$ (SEQ ID NO: 4) followed by two sites for the restriction nucleases BglII and KpnI, the nucleotide sequence encoding the tetranectin polypeptide sequence for Glu 1 to Lys 52 (SEQ ID NO: 5) followed by recognition sites for the three restriction endonucleases BamHI, HindIII, and EcoRI, respectively, and tripb, comprising nucleotide sequences encoding an IQGR cleavage site for the restriction protease $FX_a$ (SEQ ID NO: 4) followed by two sites for the restriction nucleases BglII and KpnI, the nucleotide sequence encoding the tetranectin polypeptide sequence for Glu 1 to Val 49 (SEQ ID NO: 6) followed by recognition sites for the three restriction endonucleases BamHI, HindIII, and EcoRI, respectively, were subcloned into the plasmid pT7H6 (Christensen et al., 1991), yielding pTtripa and pTtripb, respectively (FIGS. 3 and 4).

Example 2

Tetranectin, Localisation of the Trimerising Structural Element and Stability of the Triple Alpha Helical Coiled Coil The cDNA encoding the reading frame corresponding to the mature tetranectin single chain (SEQ ID NO: 7) was cloned by specific amplification in a Polymerase Chain Reaction (PCR) (Saiki et al., 1988) of the nucleotide sequences from amino acid residue Glu1 to Val181 using $1^{st}$ strand oligo-dT primed cDNA synthesized from total human placental RNA as template. Primers used in the PCR were SEQ ID NO: 8 and SEQ ID NO: 9. RNA extraction and cDNA synthesis were performed using standard procedures. The amplified reading frame encoding the monomer subunit of tetranectin was at the 5'-end, via the PCR-reaction, linked to nucleotide sequences encoding the amino acid sequence SEQ ID NO: 10 which constitute an IEGR cleavage site for the bovine restriction protease $FX_a$ (Nagai, and Thøgersen, 1987). A glycine residue was, due to the specific design of the 5'-PCR primer (SEQ. ID NO. 8), inserted between the C-terminal arginine residue of the $FX_a$ cleavage site (SEQ ID NO. 10) and the tetranectin Glu1-residue. The amplified DNA fragment was subcloned into the *E. coli* expression vector $pT_7H_6$ (Christensen et al., 1991) producing the plasmid $pT_7H_6$FX-TN123 expressing the tetranectin monomer H6FXTN123 (SEQ ID NO: 25) and into $pT_7$CIIH$_6$, which is a derivative of $pT_7H_6$, where the amino-terminal 32 amino acid residues of the lambda CII protein (SEQ ID NO: 11) are inserted 5' of the six histidine residues (SEQ ID NO: 12) as outlined in FIG. 5, yielding $pT_7$CIIH$_6$FX-TN123 expressing the tetranectin fusion protein CIIH6FXTN123 (SEQ ID NO: 24). The amino acid sequence of the expressed proteins are shown in FIG. 6 (in SEQ ID NO: 7 is given the amino acid sequence of the mature tetranectin protein). Furthermore three additional derivatives of tetranectin were constructed (FIG. 8): H6FXTN12 comprising the tetranectin amino acid residues Glu1 to Val49 (SEQ ID NO: 6), H6FXTN23 comprising the tetranectin amino acid residues Val17 to Val181 (SEQ ID NO: 7), and H6FXTN3 (SEQ ID NO: 30) comprising the tetranectin amino acid residues Ala45 to Val181 (SEQ ID NO: 7). These three tetranectin derivatives were constructed by specific amplification in a PCR using $pT_7H_6$FX-TN123 as template and the primer-pairs SEQ ID NO: 8 and SEQ ID NO: 13, SEQ ID NO: 14 and SEQ ID NO: 9, and SEQ ID NO: 15 and SEQ ID NO: 9, respectively. The amplified DNA fragments were subcloned into the *E. coli* expression vector $pT_7H_6$ producing the plasmids $pT_7H_6$FX-TN12, $pT_7H_6$FX-TN23, and $pT_7H_6$FX-TN3, respectively (FIG. 7).

To prepare recombinant tetranectin and its derivatives, each of the plasmids $pT_7H_6$FX-TN123, $pT_7$CIIH$_6$FX-TN123, $pT_7H_6$FX-TN12, $pT_7H_6$FX-TN23, and $pT_7H_6$FX-TN3 were grown in medium scale (4×1 liter; 2×TY medium, 5 mM MgSO$_4$ and 100 µg ampicillin) in *E. coli* BL21 cells, as described by Studier et al. (1990). Exponentially growing cultures at 37° C. were at OD$_{600}$ 0.8 infected with bacteriophage lambda CE6 at a multiplicity of approximately 5. Cultures were grown at 37° C. for another three hours and the cells harvested by centrifugation.

Cells were resuspended in 150 ml of 0.5 M NaCl, 10 mM Tris-HCl pH 8, and 1 mM EDTA pH 8. Phenol (100 ml adjusted to pH 8) was added and the mixture sonicated to extract the total protein. Protein was precipitated from the phenol phase by 2.5 volumes of ethanol and centrifugation.

The protein pellet was dissolved in a buffer containing 6M guanidinium chloride, 50 mM Tris-HCl pH 8 and 0.1 M dithioerythriol. Following gel filtration on Sephadex G-25 (Pharmacia, Sweden) into 8 M Urea, 1 M NaCl, 50 mM Tris-HCl pH 8 and 10 mM 2-mercaptoethanol, the crude protein preparation was applied to a $Ni^{2+}$ activated NTA-agarose column ($Ni^{2+}$NTA-agarose, 75 ml pre-washed with 8 M urea, 1 M NaCl, 50 mM Tris-HCl pH 8, and 10 mM 2-mercaptoethanol) for purification (Hochuli et al., 1988) and refolding of the fusion proteins, H6FXTN123, CIIH6FXTN123, H6FXTN12, HGFXTN23, and H6FXTN3.

For this study we chose to prepare our own $Ni^{2+}$NTA-agarose matrix. A carbodiimide coupling of the N-(5-amino-1-carboxypentyl) iminodiacetic acid metal ligand (synthesis route as described by Döbeli & Hochuli (EP-A-0 253 303)) to a rigid agarose matrix (Sepharose CL-6B, Pharmacia, Sweden) was performed:

8 g of N-(5-amino-1-carboxypentyl)iminodiacetic acid from the synthesis procedure in 50 ml was adjusted to pH 10 by addition of 29 g of Na$_2$CO$_3$(10 H$_2$O) and added to a stirred suspension of activated Sepharose CL-6B in 1 M Na$_2$CO$_3$. Reaction was allowed overnight. The Sepharose CL-6B (initially 100 ml suspension) was activated after removal of water by acetone with 7 g of 1,1'-carbonyldiimidazol under stirring for 15 to 30 min. Upon activation the Sepharose CL-6B was washed with acetone followed by water and 1 M Na$_2$CO$_3$.

The NTA-agarose matrix was loaded into a column and "charged" with $Ni^{2+}$ by slowly passing through 5 column volumes of a 10% NiSO$_4$ solution. The amount of $Ni^{2+}$ on the NTA-agarose matrix, prepared by this procedure, has been determined to 14 µmol per ml matrix. After charging the $Ni^{2+}$NTA-agarose column was washed with two column volumes of water, one column volume of 1 M Tris-HCl pH 8 and two column volumes of loading buffer before stirred mixing of the $Ni^{2+}$NTA-agarose matrix with the crude protein extracts in a breaker for 15 to 30 min. All buffers prepared for liquid chromatography were degassed under vacuum prior to addition of reductant and/or use.

The $Ni^{2+}$NTA-agarose matrix—crude extract mixture was packed in standard glass columns for liquid chromatography (internal diameter: 2.6 cm) to a volume of approximately 40 ml. The columns were washed with 200 ml of 8 M urea, 1 M NaCl, 50 mM Tris-HCl pH 8, and 10 mM 2-mercaptoethanol (Buffer I) and 100 ml 6 M guanidinium chloride, 50 mM Tris-HCl pH 8 and 10 mM 2-mercaptoethanol (Buffer II) and the adsorbed tetranectin derived fusion proteins H6FXTN123, H6CIIFXTN123, H6FXTN23, and H6FXTN3 refolded using the cyclic refolding procedure as described (Thøgersen et al., WO 94/18227).

The fusion protein H6FXTN12 was refolded by removing the guanidinium chloride and 2-mercaptoethanol of buffer II in a gradient over 5 column volumes into 50 mM Tris-HCl pH 8 and 0.5 M NaCl. After completion of the refolding procedures the tetranectin derived fusion proteins were eluted from the $Ni^{2+}$NTA-agarose columns with a buffer containing 0.5 M NaCl, 50 mM Tris-HCl, 25 mM EDTA pH 8. The tetranectin fusion proteins H6FXTN123, H6FXTN23, and H6FXTN3 were cleaved with $FX_a$ at 4° C. overnight in a molar ratio of 1:300. After $FX_a$ cleavage the protein samples were concentrated 10 fold by ultrafiltration on YM10 membranes (Amicon). After ten times dilution of the protein sample with 2 mM CaCl$_2$, the recombinant tetranectin derivatives TN123, TN23, and TN3 were isolated by ion-exchange chromatography on Q-Sepharose (Pharmacia, Sweden) in a linear gradient over 10 column volumes from 10 mM Tris-HCl pH 8, 2 mM CaCl$_2$ to 10 mM Tris-HCl pH 8, 2 mM CaCl$_2$, and 0.5 M NaCl. After elution from the Ni$^{2+}$NTA-agarose columns the fusion proteins H6CIIFXTN123 and H6FXTN12 were likewise concentrated 10 fold by ultrafiltration on YM10 membranes and gelfiltrated into buffer containing 25 mM Tris-HCl pH 8, 25 mM NaCl, and 2 mM CaCl$_2$, before purification of correctly folded monomer by ion-exchange chromatography on Q-Sepharose as described.

Recombinant full length tetranectin (TN123) produced by these procedures have been analyzed with respect to binding to plasminogen kringle 4 and immobilised fucoidan, expression of antigenic sites, and localization of disulphide bridges. In all criteria tested the produced TN123 behaved identically to isolated naturally human tetranectin (data not shown). Furthermore TN123 and TN3 have been crystallized (Kastrup et al., 1996) and the structure has also been determined, all of which bear evidence that a single unique and biologically active folded product had indeed been produced.

Analytical Gelfiltration Analysis of rTN Proteins.

Analytical gelfiltration of the recombinant tetranectin derivatives TN123, TN3, and TN23 (FIG. 9) were performed on a Superose 12 HR 10/30 column (Pharmacia, Sweden) with a total volume of 25 ml in 100 mM NaCl and 50 mM Tris-HCl pH 8 and a flow rate of 0.2 ml/min. The K$_{av}$ value is defined by, $$K_{av}=(Ve-Vo)/(Vc-Vo).$$

The gelfiltration analysis of TN123 and TN23 show that both proteins are exclusively found as trimers in solution (K$_{av}$ values of 0.27 and 0.29, respectively), whereas TN3 appeared monomeric (K$_{av}$: 0.41).

Chemical Cross-Linking of Tetranectin and Derivatives

The recombinant tetranectin derivatives TN123, TN3, and TN23, together with the fusion proteins CIIH6FXTN123 and H6FXTN12 or mixtures of these derivatives at 1 mg/ml concentrations in cross-linking buffer (0.1 M Sodium borate, pH 9.1) were incubated with dimethylsuberimidate (DMSI, Sigma). 10 µl aliquots of protein solution were incubated with 1 µl aliquots of DMSI stock solution (20 mg/ml in cross-linking buffer) for 30 minutes at 25° C. before addition of 2 µl quenching buffer (3 M Tris-HCl, pH 9). Subunit exchange between pre-formed homo-oligomers was induced by subjecting protein mixtures to heat shock treatment. Five µl aliquots of each protein solution (1 mg/ml stocks) were mixed at 0° C. in standard polypropylene microcentrifuge tubes, transferred to a water bath at 70° C. for the time spans indicated, and then further incubated for 15 minutes at 25° C. before reaction with DMSI.

Prior to analysis by SDS-PAGE (12% gels) of the cross-linked products the reaction samples were boiled in the presence of SDS and mercaptoethanol.

Cross-linking analysis of TN123 and the fusion protein CIIH6FXTN123 showed that no detectable subunit exchange between pre-formed homo-oligomers in a mixture of TN123 and CIIH6FXTN123 was found after 16 hours at room temperature (FIG. 10). Subunit exchange could be induced by incubating the protein mixture at 70° C. for 15 seconds or longer before cooling to room temperature and addition of DMSI. SDS-PAGE analysis showed the presence of four trimer bands above 95 kDa (corresponding to two homo-trimers and two hetero-trimers) and three dimer bands (corresponding to two homo-dimers and one hetero-dimer) in the gel between 43 and 55 kDa, in a relative abundance in agreement with random association of monomer subunits into trimers after subunit exchange. It should be noted, that molecular weight markers have only been included on the SDS-PAGE gels for crude calibration and orientation of the gels.

The trimeric organization of tetranectin was further corroborated by cross-linking studies of the proteins H6FXTN12, TN23, and TN3 and mixtures between them (FIG. 11). The tetranectin derivative TN3, containing only the CRD, could not be cross-linked even at high protein concentrations and did not interfere with the cross-linking of rTN123. Likewise, the derivative TN23, containing exon 2 and the CRD, appeared monomeric after cross-linking and was found not to interfere with trimerisation of TN123 during subunit exchange. Dimeric TN23 molecules found at low abundance in the sample probably reflects contaminating misfolded disulphide bridged dimers. The fusion protein H6FXTN12 formed homo-trimers upon cross-linking and generated hetero-trimers with TN123 after subunit exchange. Because of the difference in size of full length tetranectin (TN123) and H6FXTN12 the possible nine protein bands resulting from chemical cross-linking are: The four trimers [(TN123)$_3$, (TN123)$_2$(H6FXTN12), (TN123)(H6FXTN12)$_2$, and (H6FXTN12)$_3$] at approx. 95 kDa, 50 kDa, 37 kDa, and 20 kDa, respectively; the three dimers [(TN123)$_2$, (TN123)(H6FXTN12), and (H6FXTN12)$_2$] at approx. 45 kDa, 30 kDa, and 15 kDa, respectively; and the two monomers TN123 at 23 kDa and H6FXTN12 at 9 kDa.

Taken together, the gel filtration and the cross-linking analysis of the tetranectin derivatives show that tetranectin, like the collection group of C-type lectins, is a trimeric molecule and that amino acid residues directly shown to be involved in trimerisation of the tetranectin monomer are located in exon 2 of the protein (Val17-Val49). Furthermore subunit exchange between the trimeric molecules could only be observed after heat denaturation. Amino acid residues Glu1 to Asp16 of tetranectin are critical to chemical cross-linking with DMSI and more important appear to stabilize the trimeric molecule because the cross-linking analysis of the mixture TN123 and TN23 showed no decrease in TN123 formation after heat denaturation and possible subunit exchange (FIG. 11). The stability of the tetranectin trimer was corroborated by a cross-linking analysis with DMSI at different temperatures. Fifteen µl TN123 at 0.3 mg/ml concentration was pre-incubated 10 min. at either 37° C., 50° C., 60° C., or 70° C. before addition of 2 µl DMSI (20 mg/ml). The reaction was allowed to proceed for 15 min. before reaction was quenched with 5 µl of 3M Tris-HCl pH 9.1 and the reaction mixtures allowed to cool to room temperature. SDS-PAGE analysis of reduced samples (FIG. 12) showed, that trimers are readily detectable even at 60° C., although a competing pattern of cross-linking specimens increases at increasing temperatures. The appearance of other cross-linking specimens is probably due to the unfolding of the CRD. The stability of the tetranectin trimerising structural element is further analyzed using a designed chimeric protein in Example 3.

Example 3

Design and Construction of the Recombinant Chimeric Protein TRIPB-UB—the Tetranectin Trimerising Structural Element and Ubiquitin A plasmid clone, pLCMHF/UB, generously provided by Dr. O. Wiborg harbouring a human ubiquitin cDNA insert (SEQ ID: 16) was used as template and SEQ ID NO: 17 together with SEQ ID NO: 18 were used for amplification in a Polymerase Chain Reaction (PCR) (Saiki et al., 1988) of the nucleotide sequence encoding amino acid residue Ile1 to Gly76 of human ubiquitin (SEQ ID: 19). The amplified DNA fragment was after digestion with the restriction endonucleases BamHI and HindIII ligated into the BamHI and HindIII sites of pTtripb (Example 1) yielding pTtripb-UB (FIG. 13) using standard procedures.

To prepare the chimeric fusion protein H6FXtripb-UB (FIG. 14, SEQ ID NO: 31) the plasmid pTtripb-UB was grown in medium scale (4×1 liter; 2×TY medium, 5 mM $MgSO_4$ and 100 μg ampicillin) in *E. coli* BL21 cells, as described by Studier et al. (1990). Exponentially growing cultures at 37° C. were at $OD_{600}$ 0.8 infected with bacteriophage lambda CE6 at a multiplicity of approximately 5. Cultures were grown at 37° C. for another three hours and the cells harvested by centrifugation. Cells were resuspended in 150 ml of 0.5 M NaCl, 10 mM Tris-HCl pH 8, and 1 mM EDTA pH 8. Phenol 4 100 ml adjusted to pH 8) was added and the mixture sonicated to extract the total protein. Protein was precipitated from the phenol phase by 2.5 volumes of ethanol and centrifugation. The protein pellet was dissolved in a buffer containing 6 M guanidinium chloride, 50 mM Tris-HCl pH 8 and 0.1 M dithioerythriol. Following gel filtration on Sephadex G-25 (Pharmacia, Sweden) into 8 M Urea, 1 M NaCl, 50 mM Tris-HCl pH 8 and 10 mM 2-mercaptoethanol, the crude protein preparation was applied to a $Ni^{2+}$ activated NTA-agarose column for purification (Hochuli et al., 1988) and refolding of the fusion protein H6FXtripb-UB.

Synthesis and charging of the $Ni^{2+}$ activated NTA-agarose matrix is described in Example 2. All buffers for liquid chromatography were degassed prior to use. The fusion protein H6FXtripb-UB was refolded by removing the urea and 2-mercaptoethanol from buffer II in a gradient over 5 column volumes into 50 mM Tris-HCl pH 8 and 0.5 M NaCl. After completion of the refolding procedure the H6FXtripb-UB fusion protein was eluted from the $Ni^{2+}$NTA-agarose columns with a buffer containing 0.5 M NaCl, 50 mM Tris-HCl, 25 mM EDTA pH 8 and gel filtrated on a Sephadex G50 column (Pharmacia) into 0.1 M Sodium borate pH 9 buffer for chemical cross-linking analysis with DMSI.

The cross-linking analysis experiment was designed both to analyze the oligomeric status of the chimeric fusion protein and the thermal stability of the presumed fusion protein trimer as described in Example 2: Samples of 15 μl H6FXtripb-UB fusion protein, at approximately 1.0 mg/ml concentration, were pre-incubated 10 min. at either 37° C., 50° C., 60° C., or 70° C. before addition of 2 μl DMSI (20 mg/ml). The reactions were allowed to proceed for 15 min. before quenching by addition of 5 μl of 3 M Tris-HCl pH 9.1 and the reaction mixtures were allowed to cool to room temperature. SDS-PAGE analysis of reduced samples (FIG. 12) showed, (1) that the fusion protein H6FXtripb-UB is a trimer in solution (monomer at 17 kDa, dimer at 35 kDa, and trimer at 43 kDa) and (2) that a substantial amount of trimer molecules is present even at 70° C. The appearance of other larger cross-linking products is probably due to cross-linking of trimers via the ubiquitin part of the fusion protein.

Example 4

Design and Construction of Trimerised and Hexamerized CEA6 scFv Antibodies scFv(CEA6)-TRIPB, TRIPB-scFv(CEA6) and scFv(CEA6)-TRIPB-scFv(CEA6)

A plasmid clone, pUC19MCH/CEA6, generously provided by Dr. Kevin Pritchard, Cambridge Antibody Technology Ltd., Melbourn, UK, harbouring a nucleotide sequence (SEQ ID: 20) encoding the CEA6 antibody in single-chain Fv (scFv) format, followed in sequence by a "myc tag" (which is a general purification/detection handle), was used as template in Polymerase Chain Reactions (PCR) (Saiki et al., 1988) in which the nucleotide sequence encoding the scFv+myc tag was amplified using the primer pairs (SEQ ID: 21 and SEQ ID: 22) and (SEQ ID: 21 and SEQ ID: 23) to generate PCR fragments "A" and "B".

PCR fragment "A" was treated with restrictions enzymes BamHI and KpnI and the resulting fragment was inserted into BglII/KpnI cut pTripb (Example 1) to obtain the vector pTH6FXscFv(CEA6)-tripb (FIG. 15) encoding the H6FXscFv(CEA6)-TRIPE fusion protein (FIG. 16). PCR fragment "B" was treated with restriction enzymes BamHI and HindIII and the resulting fragment was inserted into BamHI and HindIII cut pTripb (Example 1) to obtain the vector pTH6FXtripb-scFv(CEA6) (FIG. 17) encoding the H6FXTRIPB-scFv(CEA6) fusion protein (FIG. 18, SEQ ID NO: 33) using standard procedures.

To generate the expression vector pTH6FXscFv(CEA6)-tripb-scFv(CEA6) (FIG. 19) encoding the H6FXscFv(CEA6)-TRIPB-scFv(CEA6) fusion protein (FIG. 20, SEQ ID NO: 34) the insert in the vector pTH6FXscFv-scFv(CEA6) was excised using restriction enzymes BamHI and HindIII and inserted into the vector pTH6FXscFv(CEA6)-tripb, which had been treated with restriction enzymes BamHI and HindIII.

To prepare the chimeric fusion proteins H6FXscFv(CEA6)-TRIPB (SEQ ID NO: 32), H6FXTRIPB-scFv(CEA6) (SEQ ID NO: 33) and H6FXscFv(CEA6)-TRIPB-scFv(CEA6) (SEQ ID NO: 34) the plasmids pTH6FXscFv(CEA6)-TRIPB, pTH6FXtripb-scFv(CEA6) and pTH6FXscFv(CEA6)-tripb-scFv(CEA6) were grown in small scale (1 liter; 2×TY medium, 5 mM MgSO4 and 100 μg ampicillin) in *E. coli* BL21 cells, as described by Studier et al. (1990). Exponentially growing cultures at 37° C. were at $OD_{600}$ 0.8 infected with bacteriophage lambda CE6 at a multiplicity of approximately 5. Cultures were grown at 37° C. for another three hours and the cells harvested by centrifugation. Cells were resuspended in 50 ml of 0.5 M NaCl, 50 mM Tris-HCl pH 8, and 1 mM EDTA pH 8. Phenol (50 ml adjusted to pH 8) was added to each and the mixtures were sonicated to extract total protein. After clarification by centrifugation (25 minutes at 10.000 g) crude protein fractions were precipitated from the phenol phases by addition of 2.5 volumes of ethanol and centrifugation. Protein pellets were dissolved in a buffer (15-25 ml) containing 6 M guanidinium chloride, 50 mM Tris-HCl pH 8 and 0.1 M dithioerythriol. Following gel filtration on Sephadex G-25 (Pharmacia, Sweden) into 8 M Urea, 1 M NaCl, 50 mM Tris-HCl pH 8 and 10 mM 2-mercaptoethanol, the crude protein preparations were applied to $Ni^{2+}$ activated NTA-agarose columns (75 ml column volume) for purification (Hochuli et al., 1988). Washing buffer (6 M guanidine-HCl, 50 mM Tris-HCl pH 8 and 10 mM 2-mercaptoethanol) was then flowed through the columns until stable baselines were obtained. Virtually pure fusion proteins could then be eluted by applying a pH gradient to each column (1000 ml gradient in 8 M urea and 10 mM 2-mercaptoethanol obtained by linear (per volume) mixing of solutions containing 50 mM sodium di-hydrogenphosphate (pH 5 buffer) and 50 mM di-sodium hydrogenphosphate (pH 8 buffer).

In preparation for in vitro refolding by the method of Thøgersen et al. (WO 94/18227) 20 mg of each purified fusion protein were mixed in suspensions in refolding "buffer B" (described below) with aliquots of suspensions of $Ni^{2+}$ activated NTA-agarose matrix sufficient to generate columns of about 75 ml packed bed volume. Each fusion protein was then subjected to the iterative refolding procedure as described for plasminogen kringle 4 in the Thøgersen et al. patent application (WO 94/18227), except that refolding of the scFv containing fusion proteins was carried out at 10° C. using a buffer containing 0.5 M NaCl, 50 mM Tris-HCl pH 8, 2 mM glutathione and 0.2 mM oxidized glutathione as "buffer A" and a buffer containing 8 M urea, 1 M NaCl, 50 mM Tris-HCl pH 8 and 2 mM glutathione as "buffer B".

After completion of the refolding procedure each column was washed with 300 ml buffer containing 0.5 M NaCl and 50 mM Tris-HCl pH 8 to wash away glutathione. The refolded fraction of each protein was then eluted from the NTA-agarose matrix by addition of 20 mM EDTA to the elution buffer. After addition of solid urea to achieve a final concentration of about 8 M to each protein sample and dilution or dialysis to reduce NaCl concentrations to below 5 mM, final purification of each correctly folded fusion protein product was then accomplished by ion exchange chromatography (S-Sepharose, Pharmacia, 1.6 (i.d.) by 90 centimeter column in a buffer containing 8 M urea, 5 mM Tris-HCl (from 1 M stock solution at pH 8) and 25 mM sodium acetate (from 1 M stock solution at pH 5), eluted at 2 ml/min). After dialysis against aqueous buffers (e.g. phosphate buffered saline) each pure and correctly refolded fusion protein was recovered in yields of 2-6 mg per liter of culture grown. Each protein may be shown by analytical gel filtration, chemical cross-linking analysis, by in vitro affinity measurements and by in vivo efficacy to form a stable homotrimeric molecular complex: The oligomeric status of the H6FXtripb-scFv-(CEA6) fusion protein was analyzed by chemical cross-linking analysis with DMSI: In parallel experiments, samples of H6FXtripb-scFv-(CEA6) at 0.34 mg/ml and TN123 at 0.28 mg/ml in 0.1 M Sodium borate were incubated at room temperature with increasing amounts (0-40 µg in 12 µl in total) of DMSI for 30 min. Reactions were quenched by addition of 5 µl 3M Tris-HCl pH 9 and the samples analyzed by SDS-PAGE under reducing conditions (FIG. 21). Like tetranectin, the H6FXtripb-scFV-(CEA6) fusion protein, of approximately 38 kDa, is hereby shown to be a trimer in solution.

REFERENCES

Berglund, L., Petersen, T. E. (1992). The gene structure of tetranectin, a plasminogen binding protein. *FEBS Lett.* 309: 15-19.
Bolivar et al, 1977. Gene, 2: 95.
Chang et al. 1978. Nature, 275: 617-624.
Christensen, J. H., Hansen, P. K., Lillelund, O., Thøgersen, H. C. (1991). Sequence-specific binding of the N-terminal three-finger fragment of transcription factor IIIA to the internal control region of a 5S RNA gene. *FEBS Lett.* 281, 181-184.
Day, A. J. (1994). The C-type carbohydrate recognition domain (CRD) superfamily. *Biochem. Soc. Trans.* 22, 83-87.
Fiers et al. 1978. Nature, 273: 113.
Fuhlendorff, J., Clemmensen, I. and Magnusson, S. (1987). Primary structure of tetranectin, a plasminogen kringle 4 binding plasma protein: Homology with asialoglycoprotein receptors and cartilage proteoglycan core protein. *Biochemistry* 26, 6757-6764.
Goeddel et al. 1979. Nature, 281: 544.
Hess et al. 1969. Advances in Enzyme Regulation, 7: 149-166.
Hitzman et al. 1980. Journal of Biological Chemistry, 25: 12073-12080.
Hochuli, E., Bannwarth, W., Döbeli, H., Gentz, R. and Stüber, D. (1988). Genetic approach to facilitate purification of recombinant proteins with a novel metal chelate adsorbent. Bio/Technology 6, 1321-1325.
Holland et al. 1978. Biochemistry, 17: 4900.
Holtet, T. L., Graversen, J. H., Thøgersen, H. C. and Etzerodt, M. (1996). Domains and shared motifs in plasminogen-ligand interaction. Poster 21st Annual Lorne Conference on Protein Structure and Function, held Melbourne, Australia, Feb. 4-8, 1996.
Itakura et al. 1977. Science, 198: 1056.
Jones. 1977. Genetics, 85: 23-33.
Kastrup, J. S. (1996). Lecture at Minisymposium held by EU HCM contract CHRX-CT93-0143: Protein Crystallography I in Hamburg, Germany, Dec. 13-14, 1996.
Kastrup, J. S., Rasmussen, H., Nielsen, B. B., Larsen, I. K., Holtet, T. L., Graversen, J. H., Etzerodt, M., Thøgersen, H. C. (1996). The human plasminogen binding protein tetranectin: Crystallization and preliminary X-ray analysis of the C-type lectin domain and the full length protein. *Acta Cryst. D* 53, 108-111.
Kingsman et al. 1979. Gene, 7: 141.
Larsen, I. K., Nielsen, B. B., Rasmussen, H. and Kastrup, J. S. (1996). Poster, 17th International Crystallography Congress, Seattle, USA held Aug. 8-17. 1996.
Nagai, K. and Thøgersen, H. C. (1987). Synthesis and sequence-specific proteolysis of hybrid proteins produced in *Escherichia coli*. *Meth. in Enzymol.* 152, 461-481.
Neame, P. J., Young, C. N, and Treep, J. T. (1992). *Prot. Sci.* 1, 161-168.
Neame, P. J. and Boynton, R. E. (1996). Protein Soc. Symposium, (Meeting date 1995; 9th Meeting: Tech. Prot. Chem VII). Proceedings pp. 401-407 (Ed., Marshak, D. R.; Publisher: Academic, San Diego, Calif.).
Nielsen, B. B. (1996). Lecture, Lundbeck Centre Neuro-Medicinal Chemistry Minisymposium held Nov. 5, 1996 at the Royal Danish School of Pharmacy, Copenhagen.
Nielsen, B. B., Larsen, I. K., Rasmussen, H. and Kastrup, J. S. (1996). Lecture, Danish Crystallographer's Meeting, held Jun. 3-4, 1996 at the Royal Danish School of Pharmacy, Copenhagen.
Saiki, R. K., Gelfand, D. H., Stoffel, S., Scharf, S. J., Higuchi, R., Horn, G. T., Mullis, K. B. and Erlich, H. A. (1988). Primer-directed enzymatic amplification of DNA with a thermostable DNA polymerase. *Science* 239, 487-491.
Siebwenlist et al. 1980. Cell, 20: 269.
Stinchomb et al. 1979. Nature 282: 39.
Studier, W., Rosenberg, A. H., Dunn, J. J. and Dubendorff, J. W. (1990). Use of T7 RNA polymerase to direct expression of cloned genes. *Meth. in Enzymol.* 185, 60-89.
Tschemper et al. 1980. Gene, 10: 157.
Wewer, U. M. and Albrechtsen, R. (1992). Tetranectin, a plasminogen kringle 4-binding protein. Cloning and gene expression pattern in human colon cancer. *Lab. Invest.* 67, 253-262.
Paul Carter and Margaret Merchant of Genentech Inc. (Current Opinion in Biotechnology, 1997, vol 8, 449-454).
Ellgaard, L., Holtet, T. L., Nielsen, P. R., Etzerodt, M., Gliemann, J. & Thøgersen, H. C. Eur J Biochem. 1997, vol 244, 544-551.
Clemmensen et al., 1986.
Clemmensen (1989) Scand J. Clin. Lab. Invest. vol 49:719-725
Review on aspects of gene therapy: Schaper, W & Ito, W. D. Current Opinion in Biotechnology, 1996, vol. 7, 635-640. Nature Biotechnology 1998 vol 16.

The invention claimed is:

1. An isolated polypeptide comprising:
   (a) a first functional amino acid sequence that is capable of forming a trimeric complex with two other first functional amino acid sequences and that has up to five amino acid substitutions at positions 10, 17, 20, 21, 24, 25, 26, 28, 29, 30, 31, 32, 33, 34, or 35 of the amino acid sequence of SEQ ID NO: 40, wherein the first functional amino acid sequence is not identical to the consensus sequence shown in SEQ ID NO: 40; and
   (b) a second functional amino acid sequence that is heterologous to the first functional amino acid sequence.

2. An isolated polypeptide comprising:
   (a) a first functional amino acid sequence that is capable of forming a trimeric complex with two other first functional amino acid sequences, wherein the first functional amino acid sequence comprises the consensus sequence of SEQ ID NO: 40; and
   (b) a second functional amino acid sequence that is heterologous to the first functional amino acid sequence, wherein the second functional amino acid sequence does not exclusively facilitate expression and/or purification of the polypeptide; and
   wherein the first functional amino acid sequence is fused to the second functional amino acid sequence and the isolated polypeptide does not consist of the amino acid sequence of SEQ ID NO: 27.

3. The isolated polypeptide of claim 1, wherein the first functional amino acid has four amino acid substitutions at positions 10, 17, 20, 21, 24, 25, 26, 28, 29, 30, 31, 32, 33, 34, or 35 of the amino acid sequence of SEQ ID NO: 40.

4. The isolated polypeptide of claim 1, wherein the first functional amino acid has three amino acid substitutions at positions 10, 17, 20, 21, 24, 25, 26, 28, 29, 30, 31, 32, 33, 34, or 35 of the amino acid sequence of SEQ ID NO: 40.

5. The isolated polypeptide of claim 1, wherein the first functional amino acid has two amino acid substitutions at positions 10, 17, 20, 21, 24, 25, 26, 28, 29, 30, 31, 32, 33, 34, or 35 of the amino acid sequence of SEQ ID NO: 40.

6. The isolated polypeptide of claim 1, wherein the first functional amino acid has one amino acid substitution at any one of positions 10, 17, 20, 21, 24, 25, 26, 28, 29, 30, 31, 32, 33, 34, or 35 of the amino acid sequence of SEQ ID NO: 40.

7. The isolated polypeptide of claim 1, wherein the second functional amino acid sequence comprises an amino acid sequence encoding all or a part of:
   (a) a ligand binding structure;
   (b) a ligand;
   (c) a receptor binding structure;
   (d) a receptor;
   (e) a detectable moiety;
   (f) an in situ activatable substance;
   (g) an enzyme; or
   (h) a cytokine.

8. The isolated polypeptide of claim 7, wherein the ligand binding structure is a receptor molecule, the ligand binding part of a receptor molecule, an antibody, an antigen binding antibody fragment, a monovalent scFv antibody fragment, a Fab antibody fragment, or a lectin.

9. The isolated polypeptide of claim 1, wherein the second functional amino acid sequence does not facilitate expression and/or purification of the polypeptide.

10. The isolated polypeptide of either claim 1 or 2, further comprising a third functional amino acid sequence that is heterologous to the first amino acid sequence.

11. The isolated polypeptide of claim 2, wherein the second functional amino acid sequence comprises an amino acid sequence encoding all or a part of:
   (a) a ligand binding structure;
   (b) a ligand;
   (c) a receptor binding structure;
   (d) a receptor;
   (e) an in situ activatable substance;
   (f) an enzyme; or
   (g) a cytokine.

12. The isolated polypeptide of claim 11, wherein the ligand binding structure is a receptor molecule, the ligand binding part of a receptor molecule, an antibody, an antigen binding antibody fragment, a monovalent scFv antibody fragment, a Fab antibody fragment, or a lectin.

13. A trimeric polypeptide complex comprising three isolated polypeptides of either claim 1 or 2.

14. The trimeric polypeptide complex of claim 13, wherein at least two of the second functional amino acid sequences are different from each other.

15. The trimeric polypeptide complex of claim 13, wherein all three of the second functional sequences are different from each other.

16. The trimeric polypeptide complex of claim 13, wherein the complex remains as a trimer at a temperature of at least 60° C.

17. The trimeric polypeptide complex of claim 13, wherein the complex remains as a trimer at a temperature of about 70° C.

18. A method for preparing the trimeric polypeptide complex of claim 13, comprising:
   (a) mixing the polypeptides;
   (b) effecting complex formation between the polypeptides; and
   (c) isolating the resulting trimeric polypeptide complex.

* * * * *